US007365850B2

(12) United States Patent
Imura

(10) Patent No.: US 7,365,850 B2
(45) Date of Patent: Apr. 29, 2008

(54) TWO-DIMENSIONAL SPECTRORADIOMETER

(75) Inventor: Kenji Imura, Toyohashi (JP)

(73) Assignee: Konica Minolta Sensing, Inc., Osaka (JP)

(*) Notice: Subject to any disclaimer, the term of this patent is extended or adjusted under 35 U.S.C. 154(b) by 0 days.

(21) Appl. No.: 11/300,778

(22) Filed: Dec. 15, 2005

(65) Prior Publication Data
US 2006/0132781 A1 Jun. 22, 2006

(30) Foreign Application Priority Data
Dec. 22, 2004 (JP) ............................ 2004-372171

(51) Int. Cl.
*G01N 21/25* (2006.01)
(52) U.S. Cl. .................. 356/419; 356/420; 356/326
(58) Field of Classification Search ............... 356/419
See application file for complete search history.

(56) References Cited

U.S. PATENT DOCUMENTS 5,424,543 A * 6/1995 Dombrowski et al. ...... 250/330
5,432,609 A 7/1995 Sugiyama et al.
5,821,535 A * 10/1998 Dombrowski et al. . 250/339.02
5,852,498 A * 12/1998 Youvan et al. .............. 356/417

FOREIGN PATENT DOCUMENTS

JP        08-050057        2/1996

* cited by examiner

Primary Examiner—Roy M Punnoose
(74) Attorney, Agent, or Firm—Brinks Hofer Gilson & Lione

(57) ABSTRACT

A two-dimensional spectroradiometer has an optical system such as an objective optical system 2 and a relay lens 6 for receiving light rays La from a two-dimensional light source L to form an optical image i.e. a first image 2a and a second image 6a, a WBPF 12 as a transmittance wavelength variable filter having a spectral transmittance characteristic that transmittance wavelengths of the light rays La differ from each other depending on transmittance sites of the filter where the respective light rays La pass, a scanning WBPF 10 which scannably holds the WBPF 12 on an optical path forming the optical image, and an image sensor 7 for capturing the second image 6a composed of the light rays La passing through the WBPF 12 at a position corresponding to each of scanning steps of the WBPF 12 to acquire a plurality of images each having a different spectral sensitivity among pixels of the image at the position corresponding to the each of the scanning steps. This arrangement enables to provide a compact and inexpensive two-dimensional spectroradiometer with shortening of the measurement time.

10 Claims, 14 Drawing Sheets

TWO-DIMENSIONAL SPECTRORADIOMETER

This application is based on Japanese Patent Application No. 2004-372171 filed on Dec. 22, 2004, the contents of which are hereby incorporated by reference.

BACKGROUND OF THE INVENTION

1. Field of the Invention

The present invention relates to a two-dimensional spectroradiometer for acquiring a spectral intensity of each pixel of a two-dimensional light source as an object for measurement, and converting the spectral intensities of the pixels into a two-dimensional distribution of an index such as luminance or chromaticity for output.

2. Description of the Related Art

Heretofore, a two-dimensional tri-stimulus colorimeter using a filter has been used to measure the luminance or chromaticity of a two-dimensional light source. In recent years, use of a surface light source having an emission spectrum approximate to a monochromatic ray, namely, having a narrow spectral bandwidth such as various display devices and LED-applied devices has been increasing, and a need for a two-dimensional spectroradiometer has been increasing in light of a demand for precise measurement of the luminance or chromaticity of such a surface light source. Many of the two-dimensional spectroradiometers are of a multi-filter type or of a type using a dispersed image through a slit, as described below.

<Multi-Filter Type>

According to a luminance measuring system, plural band pass filters (BPF) which have central wavelengths different from each other and are mounted on a rotary disk or a like device circumferentially around a rotational axis thereof are successively placed in an optical path of imaging light rays emanated from a sample such as a light source to be measured, and images composed of the light rays having transmittance wavelength bands of the respective filters are captured by a two-dimensional image sensor disposed on an imaging plane to acquire information relating to two-dimensional spectral characteristics of the sample to be measured.

<Type Using a Dispersed Image through a Slit>

According to a luminance measuring system, an image formed by an objective optical system of a two-dimensional light source, which is an object for measurement, is formed by a slit disposed on an imaging plane. The slit image, namely, a slit light source, is dispersed for each wavelength by a dispersive optical system, and the dispersed images are captured by a two-dimensional image sensor disposed on the imaging plane. Then, the object for measurement or the optical system for measurement is scanned in a direction orthogonal to the slit to acquire information relating to two-dimensional spectral characteristics of the object for measurement.

The system using the multiple filters is advantageous in the aspect of compatibility with a human eye having superior spatial resolution to wavelength resolution. However, in this case, a band pass filter of a size capable of covering the imaging light rays is necessary for each wavelength, and consequently, the size of a mechanism for successively guiding the band pass filters to the optical path of the light rays is increased. On the other hand, according to the system using a dispersed image through a slit, it is necessary to provide a mechanism for scanning the object for measurement or the optical system for measurement with an intended image resolution. In this case, it is necessary to scan the object for measurement or the optical system for measurement with such a spatial resolution that requires a large load. In any case, both of the systems unduly increase the size and the production cost of the spectroradiometer, and also unduly extend the time required for scanning, namely, the time required for measurement.

SUMMARY OF THE INVENTION

It is an object of the present invention to provide a two-dimensional spectroradiometer which is free from the problems residing in the prior art. It is another object of the invention to provide a compact, inexpensive, and easily-operable two-dimensional spectroradiometer that enables to shorten the time required for measurement.

An aspect of the invention is directed to a two-dimensional spectroradiometer comprising: an optical system which receives light from an object to be measured to form an optical image; a transmittance wavelength variable filter having a spectral transmittance characteristic that a transmittance wavelength of the light differs depending on a transmittance site of the filter where the light is passed; a scanner which movably holds the transmittance wavelength variable filter on an optical path forming the optical image for sequential scanning at a plurality of scanning positions; and an image sensor which captures the optical image composed of the light passing through the transmittance wavelength variable filter at each of the scanning positions of the filter to acquire a plurality of images having a different spectral sensitivity among pixels of the image at the each of the scanning positions.

Another aspect of the invention is directed to a method for measuring a two-dimensional spectral luminance of an object by a two-dimensional spectroradiometer provided with an optical system which receives light from an object to be measured to form an optical image, a transmittance wavelength variable filter having a spectral transmittance characteristic that a transmittance wavelength of the light differs depending on a transmittance site of the filter where the light is passed; and an image sensor which captures the optical image composed of the light passing through the transmittance wavelength variable filter. The method comprises the steps of: sequentially moving the transmittance wavelength variable filter relative to an optical path forming the optical image for sequential scanning at a plurality of scanning positions; and capturing the optical image composed of the light passing through the transmittance wavelength variable filter at each of the scanning positions of the filter to acquire a plurality of images having a different spectral sensitivity among pixels of the image at the each of the scanning positions.

These and other objects, features and advantages of the present invention will become more apparent upon reading of the following detailed description along with the accompanying drawings.

DETAILED DESCRIPTION OF THE PREFERRED EMBODIMENTS

Figure 1:
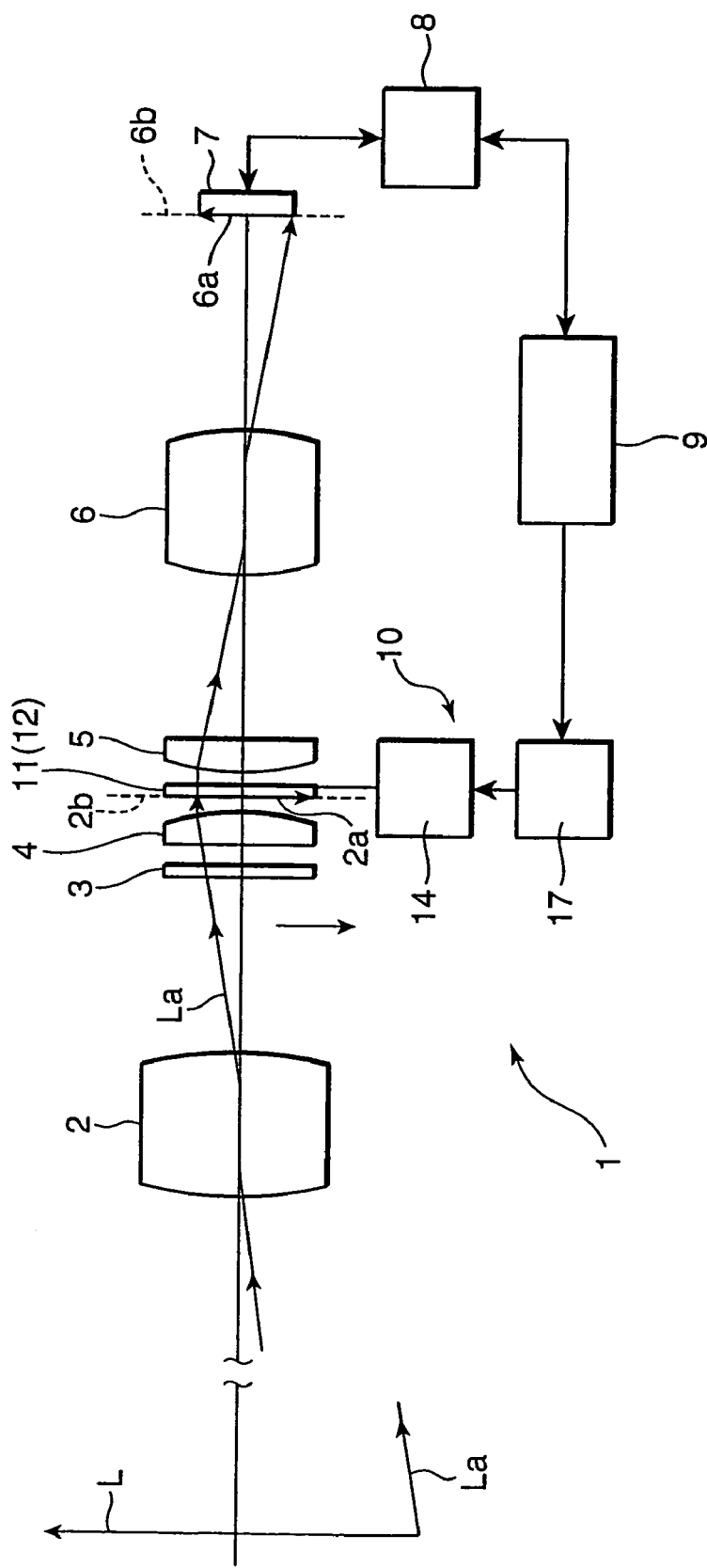
FIG. 1 is a schematic illustration showing an example of a two-dimensional spectroradiometer embodying the invention.

In the following, an embodiment of the invention is described referring to the drawings.

(Overall Description on Two-Dimensional Spectrophotometer)

FIG. 1 is a schematic illustration showing an example of a two-dimensional spectroradiometer 1 embodying the invention. The two-dimensional spectroradiometer 1 includes an objective optical system 2, a sub transmittance band removing filter 3, a first condenser lens 4, a second condenser lens 5, a relay lens 6, an image sensor 7, an image signal processor 8, a main controller 9, and a scanning wedge band pass filter 10 (hereinafter, called as "scanning WBPF 10"). The objective optical system 2 is an optical lens group for allowing light rays La from a two-dimensional light source L, which is an object for measurement, to be incident onto a first imaging plane 2b to form a first image 2a thereon. The sub transmittance band removing filter 3 is a filter for preventing rays from passing through sub transmittance bands of a WBPF 12, which will be described later. Specifically, let it be assumed that the WPBF 12 has sub transmittance bands at a wavelength position half as long as the central wavelength of an incident ray, and at a wavelength position twice as long as the central wavelength. In this case, if the central wavelength is about 400 nm, for instance, the WPBF 12 has sub transmittance bands at the wavelength position of about 200 nm, and at the wavelength position of about 800 nm. The sub transmittance band removing filter 3 is used for the WBPF 12 having such sub transmittance bands. For instance, the sub transmittance band removing filter 3 removes transmitted rays in the sub transmittance bands by blocking rays of a wavelength not larger than about 380 nm and of a wavelength not smaller than about 720 nm. The sub transmittance band removing filter 3 is disposed in front of the first condenser lens 4.

The first condenser lens 4 and the second condenser lens 5 are lens elements for collecting, namely, converging the light rays La. The first condenser lens 4 is adapted to keep the light rays La passing through the objective optical system 2 from diverging toward the WBPF 12, and to collect the light rays La passing through the objective optical system 2 onto the first imaging plane 2b. Similarly to the first condenser lens 4, the second condenser lens 5 is adapted to collect the light rays La passing through the WBPF 12 onto the relay lens 6.

The relay lens 6 is a lens element for relaying the light rays La composing the first image 2a, namely, an optical image on the first imaging plane 2b toward the image sensor 7 for life-size magnification. The light rays La passing through the relay lens 6 forms a second image 6a on a second imaging plane 6b. The focal point of the first condenser lens 4 is formed near a rear principal point of the objective optical system 2 so that principal rays of the light rays La that exit from the objective optical system 2 and compose pixels of the first image 2a for convergence are made substantially parallel to the optical axis of the optical system irrespective of the incident site of the primary rays, thereby suppressing an influence of an incident angle dependency of the central wavelength inherent to the WBPF 12. The WBPF 12 is an interference BPF and will be described later. The focal point of the second condenser lens 5 is formed near a front principal point of the relay lens 6, and is so designed as to allow the light rays La passing through the WPBF 12 to be effectively incident onto the relay lens 6.

The image sensor 7 is arranged on the second imaging plane 6b. Specifically, the image sensor 7 is arranged at such a position that an imaging plane, namely, a light receiving plane of the image sensor 7 overlaps the second imaging plane 6b to receive the light rays La forming the second image 6a on the light receiving plane of the image sensor 7 for capturing the second image 6a. The image sensor 7 has a two-dimensional imaging area, namely, the imaging plane of about 7.4 mm square e.g. 1,000×1,000 in pixels. When the light rays La are received on the imaging area of the image sensor 7, the received light amount on the imaging area is photoelectrically converted into an electrical signal for each pixel having a size of about 7.4 μm square, and the electrical signals are outputted to the image signal processor 8 as image signals.

The image signal processor 8 applies a predetermined signal processing, namely, an analog signal processing and a digital signal processing, to the image signals outputted from the image sensor 7. The image signal processor 8 has a function of converting an analog signal into a digital signal, and sends the digital signal to the main controller 9.

The main controller 9 includes a read only memory (ROM) for memorizing various control programs or the like, a Random Access Memory (RAM) for storing data for a computation process, a control process or the like, and a central processing unit (CPU) for reading out the control programs or the like from the ROM for execution. The main controller 9 controls an overall operation of the two-dimensional spectroradiometer 1.

The main controller 9 also has functions of reading images captured by the image sensor 7 in respective scanning steps by the scanning WBPF 10, which will be described later, namely, images having information relating to transmittance wavelengths different from each other among pixel arrays, as images each having a different spectral sensitivity among the pixel arrays via the image signal processor 8; performing stray light correction or luminance correction for the images based on response image information or information relating to a predetermined coefficient e.g. a calibration factor or a weighting factor, which are stored in advance in the RAM or the like, and will be described later; and performing various computations to obtain a tri-stimulus value, which will be described later. The main controller 9 may be additionally provided with a dedicated storage such as an image memory for memorizing the read images therein.

The scanning WBPF 10 is adapted to extract monochromatic rays having wavelengths different from each other from the rays transmitted through the WBPF 12. The scanning WBPF 10 extracts the monochromatic rays of the different wavelengths by relative scanning of the WBPF 12 using the light rays La by slidably and successively moving the WPBF 12, specifically, a filter support plate 11, which will be described later, in a direction perpendicular to the optical axis of the respective lens elements, namely, in x-direction (see FIG. 2) by a predetermined distance in each of the scanning steps. The scanning WBPF 10 is arranged near the first imaging plane 2b, wherein a case that the incident surface of the scanning WBPF 10 overlaps the first imaging plane 2b is included. The "scanning" by the scanning WBPF 10 means an operation of moving the WBPF 12, specifically, the filter support plate 11 relative to each light ray La whose incident site is fixed, in the scanning direction, namely, in the x-direction. The scanning WBPF 10 will be described later in detail.

The light rays La emanated from the two-dimensional light source L are incident onto the objective optical system 2, and pass through the sub transmittance band removing filter 3 for removal of rays in the sub transmittance bands. Thereafter, the light rays La excluding the rays in the sub transmittance bands are collected by the first condenser lens 4 for incidence onto the scanning WBPF 10, specifically, the WBPF 12, whereby the first image 2a is formed on the first imaging plane 2b. After forming the first image 2a, the light rays La are split while passing through the scanning WBPF 10, specifically, the WBPF 12. The spectrally separated light rays La pass through the second condenser lens 5, and enter the relay lens 6 where the first image 2a composed of the light rays La is relayed for life-size magnification, thereby forming the second image 6a on the second imaging plane 6b. Thus, the second image 6a is captured by the image sensor 7, and a signal indicating the captured image is sent to the image signal processor 8 for signal processing such as analog-to-digital (A/D) conversion. Thereafter, the digital signal is sent to the main controller 9, which, in turn, performs various computations such as removal of a stray light image from the captured image.

Figure 2:
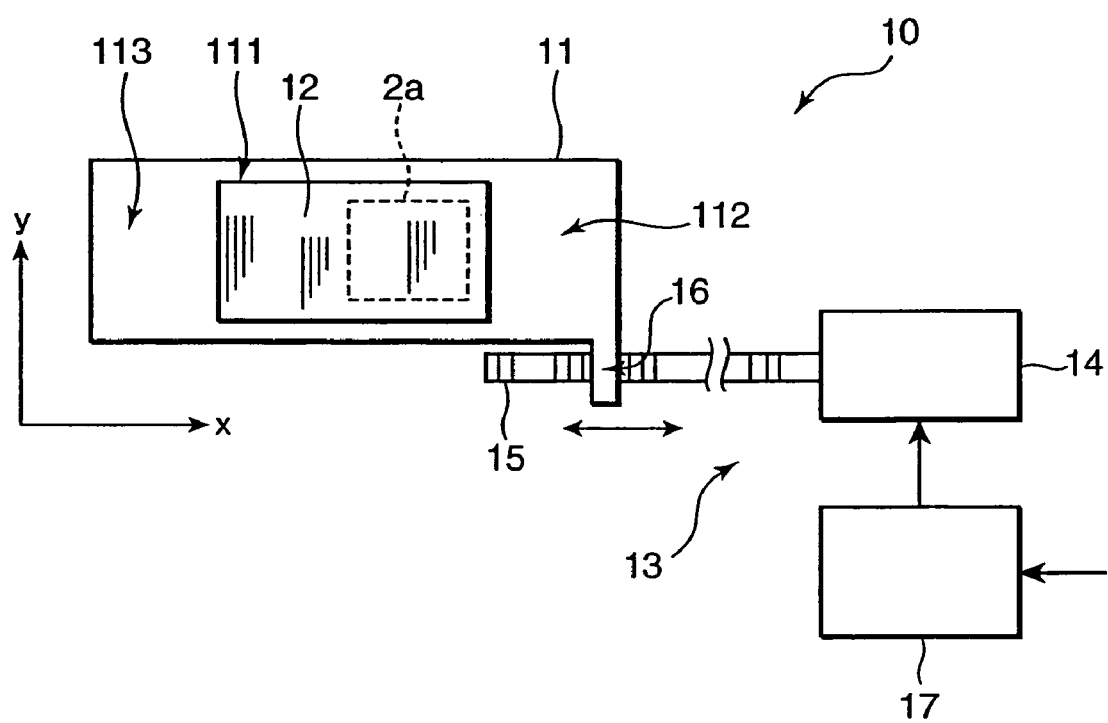
FIG. 2 is a schematic illustration showing an example of a scanning wedge band pass filter (WBPF) in the two-dimensional spectroradiometer shown in FIG. 1.

The scanning WBPF 10 is described in detail referring to FIG. 2. As shown in FIG. 2, the scanning WBPF 10 includes the filter support plate 11, the WBPF 12, and a scanning driver 13. The filter support plate 11 is designed to support the WBPF 12 thereon. The filter support plate 11 has its outer configuration shaped into a planar member of a substantially rectangular shape, which serves as a frame member of the WBPF 12. An opening 111 is formed substantially in a central portion of the filter support plate 11. The opening 111 has such dimensions that a side thereof in the x-direction, namely, in the scanning direction is about 20 mm, and a side thereof orthogonal to the x-direction, namely, in the y-direction is about 9 mm. The WBPF 12 is encased in the opening 111 by fitting or a like technique. The dotted frame within the WBPF 12 indicates a fixed site where the light rays La are allowed to pass to form an optical image on the image sensor 7. In other words, the dotted frame indicates the first image 2a to be formed on the WBPF 12. The dotted frame has such a size and shape as to match the imaging plane of the image sensor 7 e.g. a square shape of about 7.4 mm on one side.

A first light blocking portion 112 and a second light blocking portion 113 are formed on opposite side portions of the filter support plate 11 in the x-direction with the opening 111 being formed therebetween, namely, on left and right side portions thereof. The first, second light blocking portion 112, 113 has a size at least corresponding to the size of the first image 2a indicated by the dotted frame. The first, second light blocking portion 112, 113 is designed in such a manner that moving the filter support plate 11 in the x-direction to such a position that causes the first, second light blocking portion 112, 113 to overlap the imaging area where the first image 2a is formed, the first, second light blocking portion 112, 113 blocks the light rays La from being incident onto the image sensor 7. In this way, providing the first and the second light blocking portions 112 and 113 on the filter support plate 11 allows the filter support plate 11 to perform a function as a shutter for blocking light from being incident onto the image sensor 7. Thereby, the arrangement of the spectroradiometer is simplified without the need of additionally providing a shutter.

Figure 3:
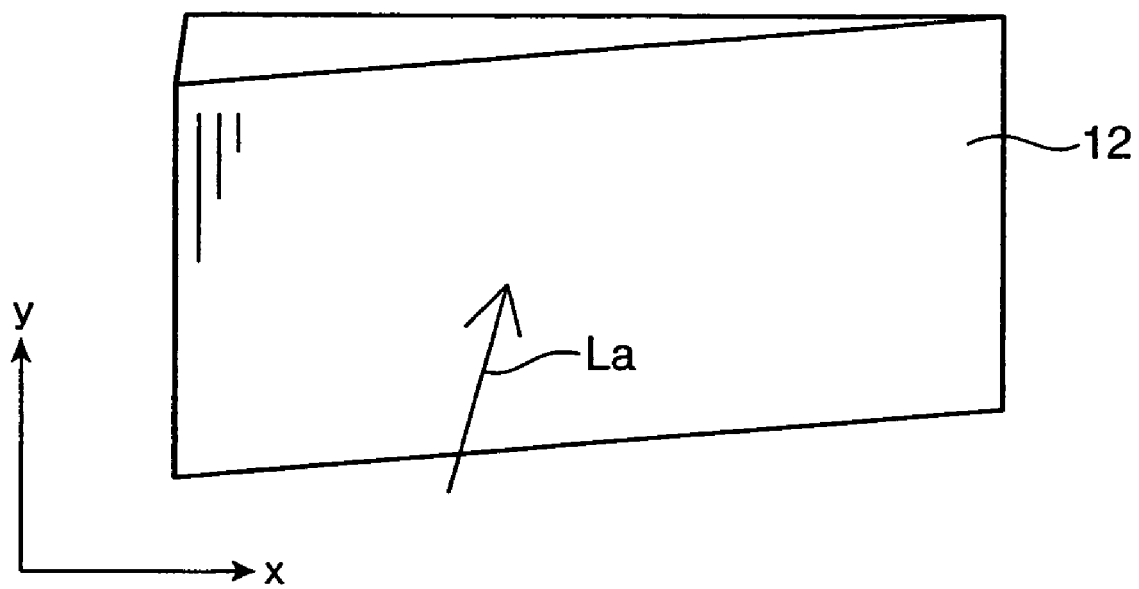
FIG. 3 is a perspective view showing an example of a WBPF.

The WBPF 12 is a filter for obtaining transmitted rays having central wavelengths different from each other in the scanning direction. Specifically, the WBPF 12 is a so-called interference band pass filter (BPF) having a characteristic that the central wavelength λ of a transmitted ray at respective coordinate positions (x, y) of the WBPF 12, namely, the central wavelength λc (x, y) is constant in the y-direction, and sequentially or smoothly varies in the x-direction by about 17 nm/mm. If the x-coordinate is expressed by using a width d(=0.296 mm), which is a distance to be moved in each scanning step, and will be described later, the central wavelength of the WBPF 12 sequentially changes from about 390 nm to about 710 nm in the scanning range of x=0 to 64·d, namely, from 0 to 18.9 mm. As shown by the WBPF 12 in FIG. 3, the WBPF 12 having a different central wavelength depending on the coordinate position is a so-called wedge interference filter, in which the filter thickness is linearly changed in the scanning direction, namely, in the x-direction.

The scanning driver 13 drivingly moves the WBPF 12 including the first and the second light blocking portions 112, 113 for scanning by moving the filter support plate 11 relative to the light rays La composing the first image 2a in the scanning direction, namely, in the x-direction. The scanning driver 13 includes a stepping motor 14, a rotary shaft 15, a linking member 16, and a driving circuit 17. The stepping motor 14 is a motor for drivingly rotating the rotary shaft 15, and rotates at a predetermined rotation speed by a predetermined rotation angle each time a pulse signal, namely, a digital signal is inputted. The linking member 16 is adapted to link the rotary shaft 15 and the filter support plate 11 so that the filter support plate 11 is movable parallel to the rotary shaft 15. The linking member 16 is secured to the filter support plate 11. In this embodiment, the linking member 16 is integrally formed with one end of the filter support plate 11 corresponding to the side of the first light blocking portion 112. As far as the filter support plate 11 is movable in the x-direction for scanning, the linking member 16 may be connected to the filter support plate 11 at any position e.g. on the side of the second light blocking portion 113, or may have an arbitrary configuration.

The rotary shaft 15 is adapted to move the linking member 16 in a linked state with the linking member 16, and a threaded portion is formed in the entire length of a shaft body of the rotary shaft 15, for instance. With this arrangement, the linking member 16 engages the rotary shaft 15. The rotary shaft 15, serves as a rotary axis of the stepping motor 14, and moves the linking member 16 in the scanning direction, namely, in the x-direction in accordance with a rotary driving of the stepping motor 14. The driving circuit 17 controls the driving of the stepping motor 14. Specifically, the driving circuit 17 controls the rotary driving of the stepping motor 14 such as a rotation angle and a rotation speed by outputting a pulse signal to the stepping motor 14 in accordance with an operated state of the stepping motor 14. The rotary driving control of the stepping motor 14 by the driving circuit 17 is performed based on a scanning drive control command signal outputted from the main controller 9.

In this way, the scanning driver 13 drives the stepping motor 14 by way of the driving circuit 17 in response to receiving the scanning drive control command signal from the main controller 9, and moves the filter support plate 11 in the plus or minus x-direction via the rotary shaft 15 and the linking member 16. The scanning by the movement of the filter support plate 11 is controlled in such a manner that a scanning step is performed by moving the filter support plate 11 by a distance of about 0.296 mm corresponding to 5 nm in pitch for the central wavelength of the WBPF 12, based on a premise that the central wavelength of the WBPF 12 varies by about 17 nm/mm.

As mentioned above, the sub transmittance band removing filter 3 is provided independently of the WBPF 12. Since the scanning driver 13 is designed to move exclusively the WBPF 12 and the filter support plate 11, the scanning load and the moving distance by the scanning driver 13 are minimized. This arrangement enables to reduce the size and the production cost of the scanning driver 13, and leads to shortening of the time required for scanning, namely, measurement.

In this embodiment, in the respective scanning steps, spectral transmittance characteristics of the BPF having 5 nm pitch, which is successively set for each pixel of the second image 6a formed on the imaging area of the image sensor 7, are weight integrated to synthesize color matching functions $x(\lambda)$, $y(\lambda)$, $z(\lambda)$ of 2-degree standard observer recommended by the International Commission on Illumination (CIE). A first-order interference BPF is adopted as the WBPF 12 to set the half-width of the central wavelength of the WBPF 12 to about 15 nm to enhance precision in synthesis. A half-width as large as 15 nm enables to enhance precision in synthesis. Generally, a first order interference BPF has a sub transmittance band in a wavelength range including the position half as long as the central wavelength of an incident ray, and in a wavelength range including the position twice as long as the central wavelength, as mentioned above.

Next, an actual scanning operation by the scanning WBPF 10, specifically, by the scanning driver 13 is described.

First, symbols to be used herein are described:

x: a coordinate on the first imaging plane 2b and on the second imaging plane 6b in the scanning direction, namely, in the x-direction where x=0 to 7.4 mm y: a coordinate on the first imaging plane 2b and on the second imaging plane 6b in the direction orthogonal to the scanning direction, namely, in the y-direction where y=0 to 7.4 mm s: a scanning position of the WBPF 12 represented by the scanning step where s=0 to 65 i, j: a yx coordinate on the first imaging plane 2b and on the second imaging plane 6b in pixel unit where i,j=1 to 1,000 j': an x-coordinate on the WBPF 12 in pixel unit where j'=1 to 2,560

$I_{ij}$: image information $(I_{ij})_s$: image information in the scanning step s As mentioned above, the scanning by the filter support plate 11, specifically, by the WBPF 12 of the scanning WBPF 10 is performed by a step width d=40·7.4 μm=0.296 mm, which corresponds to 5 nm. This step width d corresponds to 40 pixels in an array. Accordingly, the wavelength range of 320 nm(=710−390 nm) in a visible range from 390 to 710 nm of the WBPF 12 can be covered by performing the scanning step 64(=320/5) times, namely, by moving the filter support plate 11 by the distance: 64·0.296=18.9 mm, which corresponds to 64·40=2,560 pixels in an array. However, the imaging area of the image sensor 7 has a pixel array corresponding to 1,000 pixels in the x-direction, namely, a length equivalent to performing the scanning step 25 times. Therefore, it is necessary to perform the scanning step at least 89 (=64+25) times including the 25 times to scan all the pixels of the image sensor 7, namely, a pixel array of 1,000 pixels by using the wavelength width of 320 nm of the WBPF 12, in other words, to cover all the pixels on the imaging area of the image sensor 7 with the wavelength range from 390 to 710 nm. The initial position of the filter support plate 11 before start of the scanning is set as a scanning step s=0.

Figure 4:
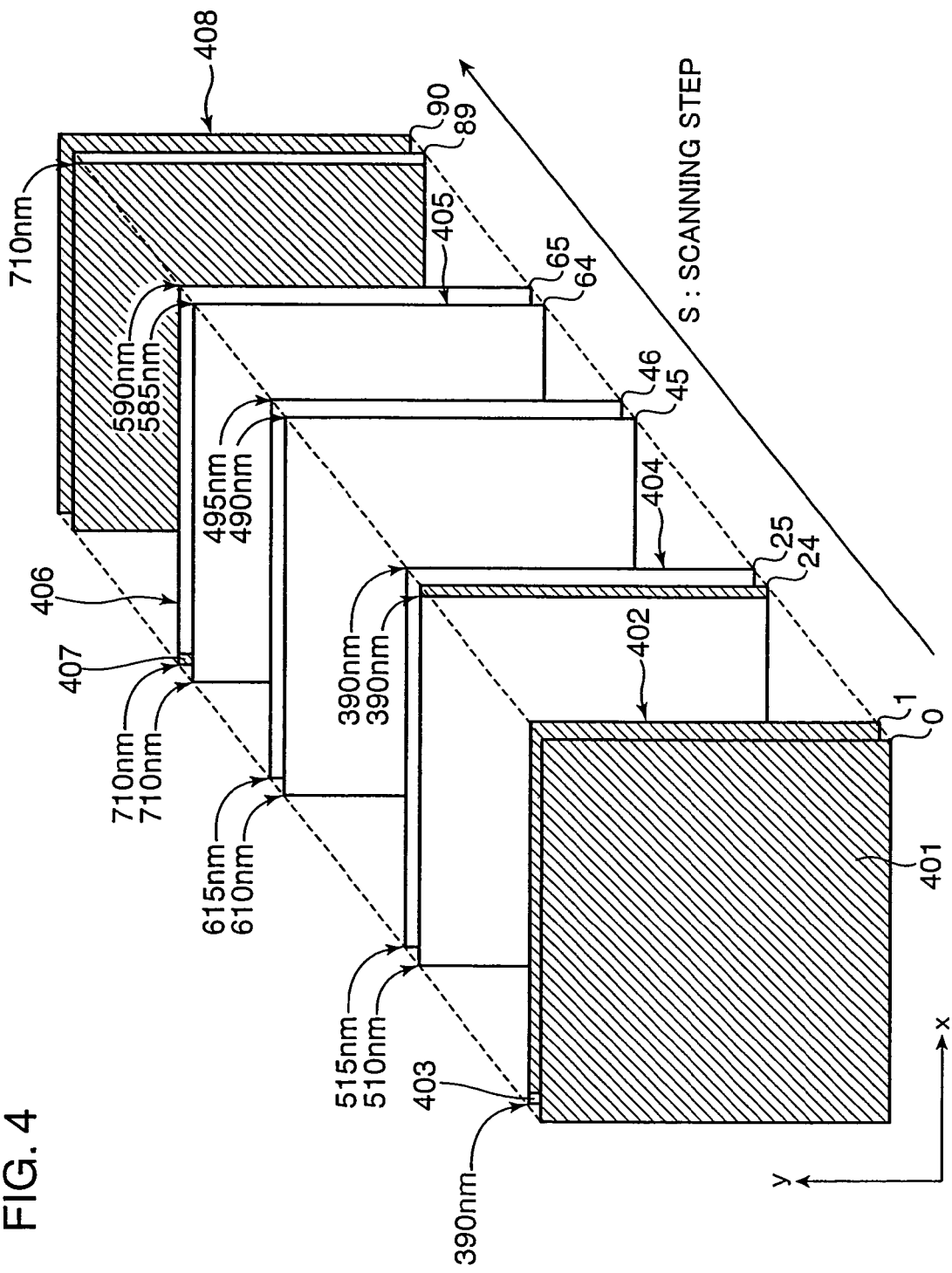
FIG. 4 is a conceptual illustration for describing images captured on an imaging area of an image sensor in respective scanning steps.
Figure 5:
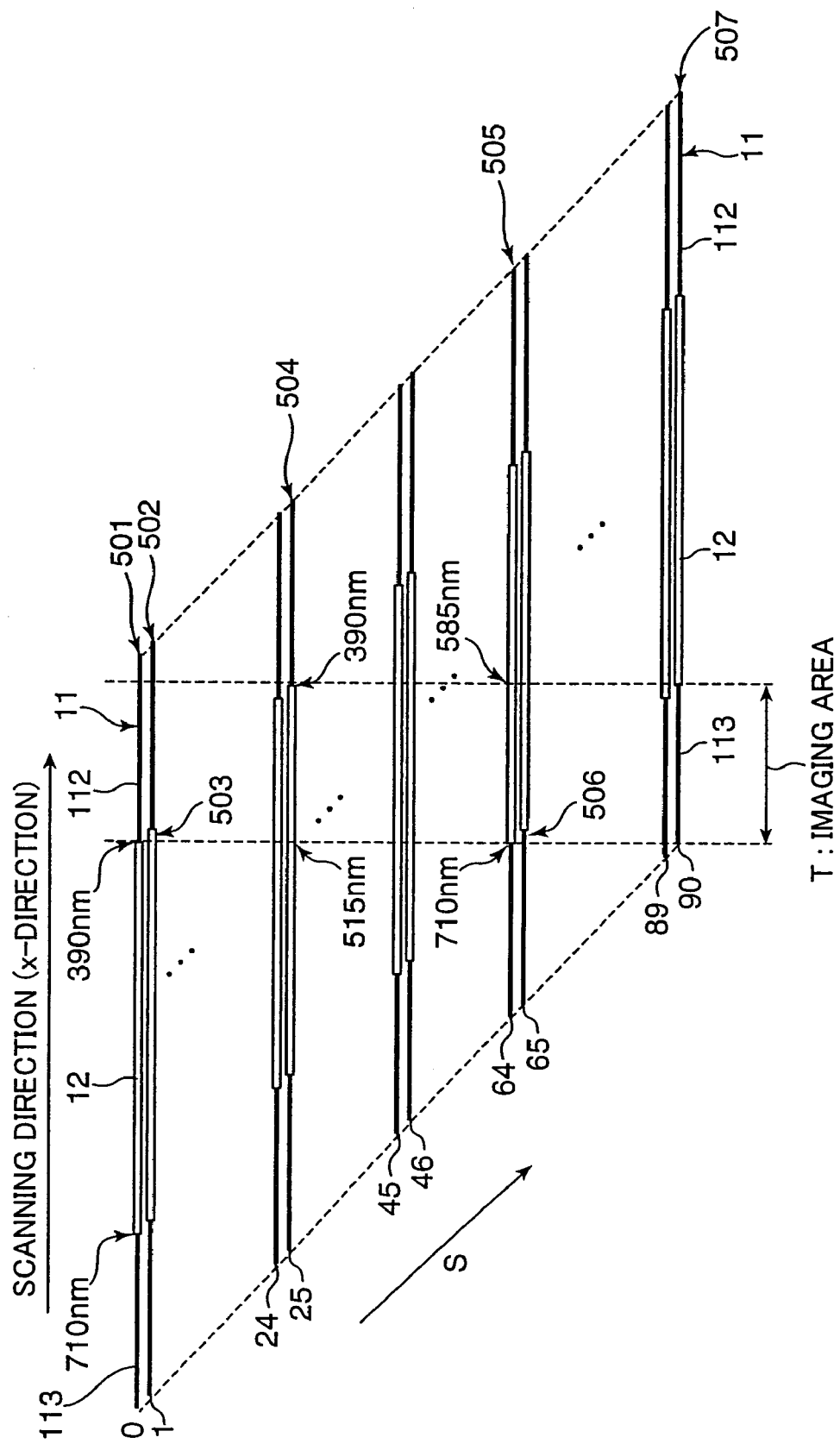
FIG. 5 is a conceptual illustration for describing a positional relation between respective parts of a filter support plate which is moved in a scanning direction, namely, in x-direction in each of the scanning steps, and the imaging area of the image sensor.

The above scanning operation is described referring to FIGS. 4 and 5. FIG. 4 is a conceptual illustration for describing an exposed state of a captured image on the imaging area of the image sensor 7 in each scanning step s. FIG. 5 is a conceptual illustration for describing a positional relation between the WBPF 12 including the first light blocking portion 112 and the second light blocking portion 113 of the filter support plate 11 that are moved in the scanning direction, namely, in the x-direction in each scanning step s, and the imaging area of the image sensor 7. As shown in FIG. 4, before scanning starts, namely, before spectral luminance measurement by the two-dimensional spectroradiometer 1 starts, the filter support plate 11, specifically, the WBPF 12 is set at the initial position (s=0) where the first blocking portion 112 of the filter support plate 11 blocks the imaging area of the first imaging plane 2b. This state corresponds to the position of the filter support plate 11 (s=0) indicated by the reference numeral 501 in FIG. 5. In this state, the first light blocking portion 112 overlaps an imaging area T having a width corresponding to a pixel array j=1 to 1,000.

When the scanning starts, a forwardmost image 401 in FIG. 4, namely, an image $(I_{ij})_0$ is captured as a dark image such as a noise image or an offset image by the image sensor 7 at the position corresponding to the scanning step s=0. Next, the scanning driver 13 moves the filter support plate 11 parallel to the rotary axis of the rotary shaft 15 and in the plus x-direction by one scanning step (1s) to the position indicated by the reference numeral 502 in FIG. 5, and a first image 402, namely, an image $(I_{ij})_1$ is captured at the position corresponding to the scanning step s=1. In the image $(I_{ij})_1$, a monochromatic ray having a central wavelength of 390 nm is incident onto the first pixel array (j=1) indicated by the reference numeral 403, which corresponds to the pixel array indicated by the reference numeral 503 in FIG. 5, while the other pixel arrays (j=2 to 1,000) are kept in a light blocking state.

Thereafter, an image is captured each time the one scanning step is performed. The pixel array j on which a monochromatic ray of the central wavelength of 390 nm is incident is shifted rightward, namely, in the plus x-direction each time the scanning step is performed, and the wavelength of the monochromatic ray incident onto the first pixel array (j=1) is incremented by about 5 nm each time the scanning step is performed. As the scanning step advances, the number of pixel arrays blocked by the first light blocking portion 112 is decreased. When the scanning step s reaches 25, the first light blocking portion 112 leaves out of the imaging area of the image sensor 7. In an image $(I_{ij})_{25}$ corresponding to an image 404 captured at the scanning step s=25, which is captured when the filter support plate 11 is moved to the position indicated by the reference numeral 504 in FIG. 5, the central wavelengths of the monochromatic rays incident onto the first through the thousandth pixel arrays (j=1 to 1,000) are sequentially changed from 390 nm to 515 nm.

When the scanning step s is increased, and an image $(I_{ij})_{64}$ corresponding to an image 405 which is captured at the scanning step s=64 is captured when the filter support plate 11 is moved to the position indicated by the reference numeral 505 in FIG. 5, the central wavelengths of the monochromatic rays incident onto the first through the thousandth pixel arrays are sequentially changed from 585 nm to 710 nm. At the scanning step s=65, the first pixel array (j=1) indicated by the reference numeral 407 in an image 406, which is the same pixel array as indicated by the reference numeral 403, and corresponds to the pixel array indicated by the reference numeral 506 in FIG. 5, is blocked by the second light blocking portion 113. When the scanning step s is increased furthermore, the light blocking area to be blocked by the second light blocking portion 113, namely, the number of pixel arrays to be blocked, is increased. At the final scanning step s=90, which corresponds to the position of the filter support plate 11 indicated by the reference numeral 507 in FIG. 5, the entire imaging area (j=1 through 1,000) is blocked by the second light blocking portion 113, as shown by an image 408, which is a dark image similar to the image 401. In this way, the filter support plate 11 and the WBPF 12 are moved in the scanning direction step by step by the scanning WBPF 10, specifically, by the scanning driver 13, and the captured image by the image sensor 7 is read each time the scanning step is performed. Alternatively, the captured image at the scanning step s=90 may not be read because the dark image has already been acquired in the scanning step s=0.

The above description shows that the captured images in the respective scanning steps s have a characteristic that the central wavelength of the monochromatic ray incident on the respective pixels of each one of the captured images has dependency on the scanning step s and on the x-coordinate of the corresponding pixel, and that the central wavelength is sequentially changed in the x-direction, namely, in the direction of the column number j, while the central wavelength is kept substantially unchanged in the y-direction, namely, in the direction of the row number i.

(Processing of Spectral Image Information)

The two-dimensional spectroradiometer 1 obtains a tri-stimulus image based on the image $(I_{ij})$ captured by the respective scanning steps s for output. Generally, in a multi-band calorimeter, color matching functions x(λ), y(λ), z(λ) of 2-degree standard observer recommended by the CIE are synthesized by multiplying spectral sensitivities of the image different from each other by an appropriate weighting factor for integration. In a two-dimensional light measuring apparatus such as the two-dimensional spectroradiometer 1, the above process is executed with respect to each of the pixels.

In the following, description is made as to how the tri-stimulus image is obtained based on the image $(I_{ij})_s$.

The image $(I_{ij})_s$ obtained in the respective scanning steps s is converted into a luminance image $(L_{ij})_s$ using a luminance calibration factor $(C_{ij})_s$, for each of the pixels. The luminance calibration factor $(C_{ij})_s$ is known by conducting a luminance axis calibration, which will be described later. If weighting factors to be applied to the luminance image $(L_{ij})_s$ to obtain a tri-stimulus value are $Wx_{sj}$, $Wy_{sj}$, $Wz_{sj}$, the tri-stimulus value $X_{ij}$, $Y_{ij}$, $Z_{ij}$ is calculated by performing the following equations (1-1) through (1-3).

$$X_{ij} = \Sigma_s Wx_{sj} \cdot (L_{ij})_s \qquad (1\text{-}1)$$

$$Y_{ij} = \Sigma_s Wy_{sj} \cdot (L_{ij})_s \qquad (1\text{-}2)$$

$$Z_{ij} = \Sigma_s Wz_{sj} \cdot (L_{ij})_s \qquad (1\text{-}3)$$

Generally, according to a spectral luminance measurement using a multi-filter system (see the Description of the Related Art), light rays in wavelength bands identical to each other are incident onto all the pixels constituting one image. Whereas the same weighting factor is applied to all the pixels in the conventional spectroradiometer using the multi-filter system, according to the technique in the embodiment, the weighting factor differs among the pixels, because the transmittance wavelength band of the incident ray differs in each scanning step s and for each pixel array.

Also, it is possible to obtain in advance weighting factors $Wx_{s,ij}$, $Wy_{s,ij}$, and $Wz_{s,ij}$ for each pixel of an acquired image in each scanning step based on the luminance calibration factor $(C_{ij})_s$ and on the weighting factors $Wx_{sj}$, $Wy_{sj}$, and $Wz_{sj}$, and to calculate the tri-stimulus value $X_{ij}$, $Y_{ij}$, and $Z_{ij}$ by performing the equations (2-1) through (2-3). The altered technique enables to further shorten the time required for calculating the tri-stimulus value.

$$X_{ij} = \Sigma_s Wx_{s,ij} \cdot (I_{ij})_s \qquad (2\text{-}1)$$

$$Y_{ij} = \Sigma_s Wy_{s,ij} \cdot (I_{ij})_s \qquad (2\text{-}2)$$

$$Z_{ij} = \Sigma_s Wz_{s,ij} \cdot (I_{ij})_s \qquad (2\text{-}3)$$

The above integration is implemented each time the scanning step is performed, and at the time when the scanning is completed, a tri-stimulus image is obtained. The tri-stimulus image is saved or stored in the RAM or the like in the main controller 9. This method is advantageous in remarkably reducing a data storage capacity necessary for data storage and processing, as compared with a method in which eighty-nine monochromatic images acquired by performing image capturing operations while successively changing the wavelength by 5 nm pitch, namely, captured images obtained by performing the scanning step s=1 to 89 shown in FIG. 4 are saved and converted altogether into a tri-stimulus image after the scanning is completed.

Figure 11:
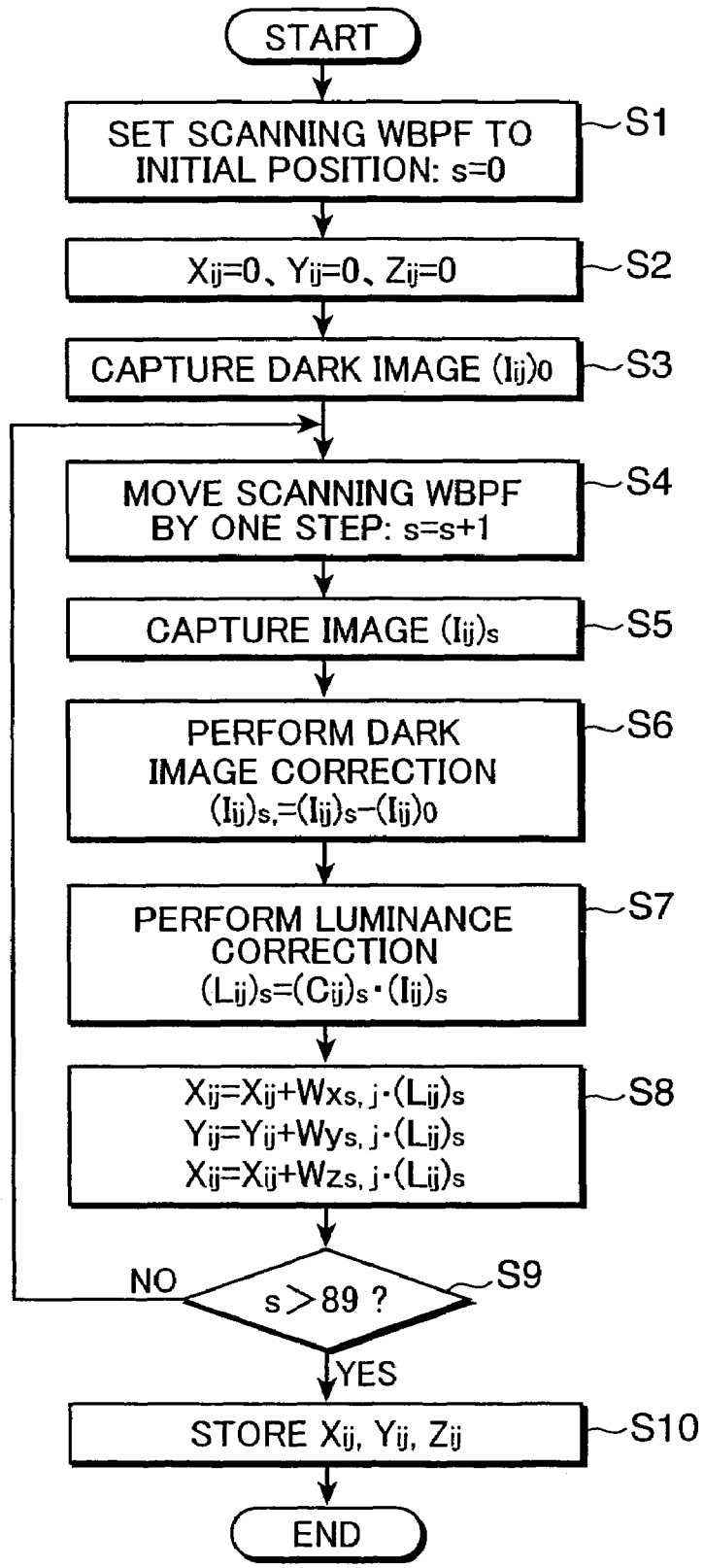
FIG. 11 is a flowchart showing an example of an operation concerning measurement of a tri-stimulus image by the two-dimensional spectroradiometer.

FIG. 11 is a flowchart showing an example of an operation in measuring a tri-stimulus image by the two-dimensional spectroradiometer 1. First, the scanning WBPF 10, specifically, the filter support plate 11 is set to the initial position (s=0) by the scanning driver 13 under the control of the main controller 9 (Step S1). Then, the initial value of the tri-stimulus value $X_{ij}$, $Y_{ij}$, and $Z_{ij}$ is set to 0 (Step S2). At the scanning step s=0, a dark image $(I_{ij})_0$ obtained in a state that the imaging area of the image sensor 7 is blocked is outputted to the main controller 9 via the image signal processor 8 (Step S3). Subsequently, the scanning WBPF 10, specifically, the filter support plate 11 is moved by one scanning step (Step S4), and an image $(I_{ij})_s$ at the scanning step s=1 is captured and sent to the main controller 9 (Step S5). Then, the main controller 9 performs dark image correction: $(I_{ij})_s = (I_{ij})_s - (I_{ij})_0$ using the dark image $(I_{ij})_0$ acquired in Step S3 (Step S6). Thereafter, luminance correction: $(L_{ij})_s = (C_{ij})_s \cdot (I_{ij})_s$ is performed for the image $(I_{ij})_s$ after the dark image correction, using the luminance correction factor $(C_{ij})_s$, which is calculated by performing luminance axis calibration to be described later and saved in the RAM or the like in the main controller 9, whereby the image $(I_{ij})_s$ is converted into a luminance image $(L_{ij})_s$ (Step S7).

Then, the luminance image $(L_{ij})$ is multiplied by the weighting factors $Wx_{sj}$, $Wy_{sj}$, and $Wz_{sj}$ of the respective stimulus values, which are different among the pixel arrays of the captured image, for integration, namely, equations: $X_{ij}=X_{ij}+Wx_{sj} \cdot (L_{ij})_s$, $Y_{ij}=Y_{ij}+Wy_{sj} \cdot (L_{ij})_s$, and $Z_{ij}=Z_{ij}+Wz_{sj} \cdot (L_{ij})_s$ are performed each time the scanning step is performed (Step S8). If the main controller 9 judges that the scanning step s is not larger than 89 (NO in Step S9), the routine returns to Step S4, and the operations from Steps S5 through S8 are repeated for a next scanning step s after the scanning WBPF 10 is moved by one scanning step. In Step S8 during repeating the operations from S5 through S8, update of the integrated value, namely further integration of the tri-stimulus value $X_{ij}$, $Y_{ij}$, and $Z_{ij}$ obtained in the previous scanning step is performed. If the main controller 9 judges that the scanning step s is larger than 89 (YES in Step S9), the tri-stimulus image ($X_{ij}$, $Y_{ij}$, and $Z_{ij}$) obtained by the integration as a result of performing all the scanning steps s is stored in a predetermined data storage such as the RAM in the main controller 9 (Step S10). Then, the flow ends.

In the embodiment described in the flowchart of FIG. 11, stray light correction, which will be described later, is not performed for the acquired image $(I_{ij})_s$. Even if the stray light correction is not performed, it is possible to store the image $(I_{ij})_s$ acquired in each scanning step s, to convert the acquired image $(I_{ij})_s$ into a luminance image $(L_{ij})_s$ using a luminance correction factor $(C_{ij})_s$ for each pixel (see the equation (6-1) to be described later), and to obtain a spectral luminance image $L_{ij}(\lambda)$, which will be described later, by performing a well-known computation process, using relative spectral sensitivity $S_{sj}(\lambda)$ of each pixel array j, which is known by performing the wavelength axis calibration to be described later.

In the two-dimensional spectroradiometer 1, the wavelength axis calibration and the luminance axis calibration are performed for the WBPF 12 in advance e.g. before shipment. Data for computation such as the luminance calibration factor $(C_{ij})_s$ acquired by the above calibration, for instance, is stored in the RAM or the like in the main controller 9. In actual spectral luminance measurement, a captured image, namely an observed image is converted into a luminance image, namely, luminance correction is performed, using the data for computation. In the following, the wavelength axis calibration and the luminance axis calibration are described.

(Wavelength Axis Calibration)

Figure 6:
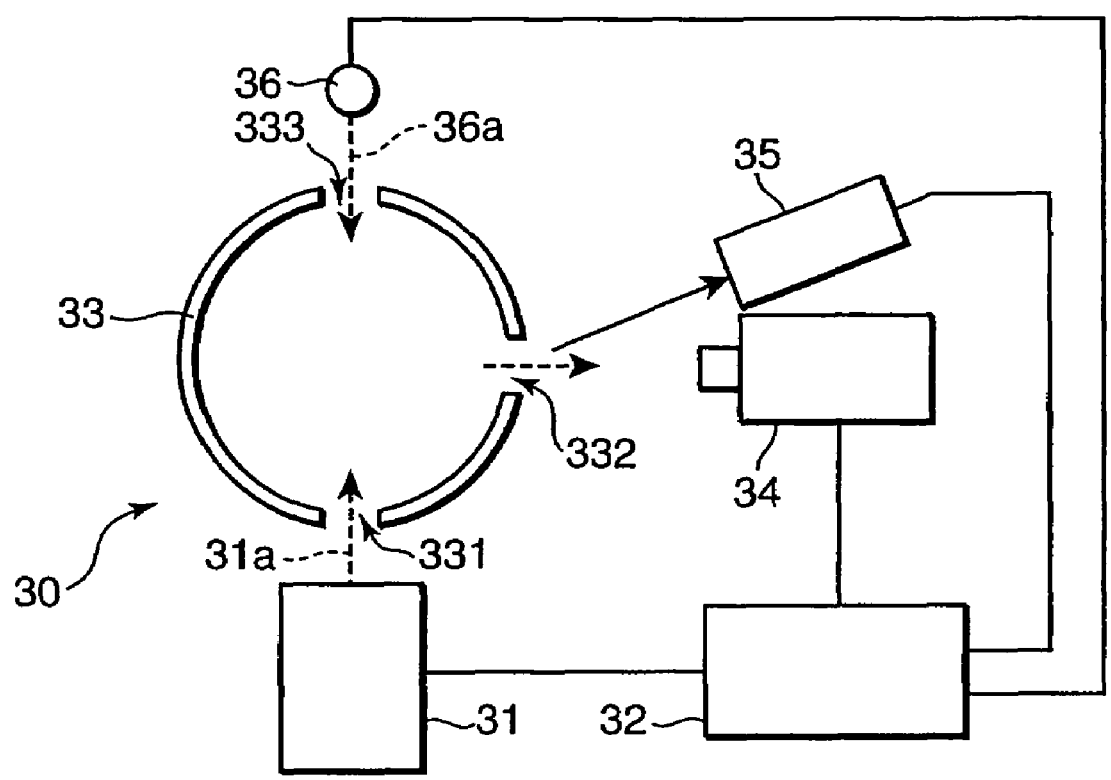
FIG. 6 is a schematic illustration showing an example of a calibration system for wavelength axis calibration.

Wavelength axis calibration for the WBPF 12 is performed by obtaining a reference intensity $M_\lambda$ using a calibration system 30 as shown in FIG. 6 for instance, and by obtaining a spectral sensitivity of each pixel array j in each scanning step s by the two-dimensional spectroradiometer 1 based on the reference intensity $M_\lambda$. Specifically, in the calibration system 30, a reference mono-wavelength light source 31 is controlled by a personal computer (PC) 32 designed for controlling, so that two-hundred and one monowavelength rays 31a in total each having a sufficiently narrow half-width ranging from 350 nm to 750 nm with 2 mn pitch, for instance, are outputted into an integrating sphere 33 through an incident aperture 331. The monowavelength rays 31a are multi-diffused and multi-reflected within the integrating sphere 33 to form a uniform luminance surface on an output aperture 332 of the integrating sphere 33. A two-dimensional spectroradiometer 34 to be calibrated, as an example of the two-dimensional spectroradiometer 1, acquires image information relating to a mono-wavelength image composed of each of the monowavelength rays 31a by measuring the uniform luminance surface, and sends the acquired image information to the PC 32. The uniform luminance surface formed by the multidiffusion and the multi-reflection of the mono-wavelength rays 31a is also measured by a spot-type reference spectroradiometer 35. Information relating to the reference intensity $M_\lambda$ acquired by the reference spectroradiometer 35 is also sent to the PC 32. The element denoted by the reference numeral 36 in the calibration system 30 is a white light source for outputting white rays 36a to be incident onto the integrating sphere 33, in place of the mono-wavelength rays 31a emanated from the reference mono-wavelength light source 31, in the luminance axis calibration to be described later. The white light source 36 is not used in the wavelength axis calibration. Therefore, the white light source 36 and an incident aperture 333 of the integrating sphere 33 may be omitted in the wavelength axis calibration.

As described in FIGS. 4 and 5, the effective area of the WBPF 12 in the scanning direction corresponds to 2,560 pixel arrays (j'=1 to 2,560), and is larger in size than the imaging area of the image sensor 7 having 1,000 pixel arrays (j=1 to 1,000). Accordingly, it is impossible to measure the entire effective area of the WBPF 12 by an image capturing operation at a single scanning position. In view of this, the spectral sensitivity on the entire effective area of the WBPF 12 is obtained with respect to each pixel by performing the scanning using the mono-wavelength rays 31a from the reference mono-wavelength light source 31, namely, rays from the uniform luminance surface at three different scanning positions corresponding to the scanning step s=25, 45, and 65.

First, for calibration of the two-dimensional spectroradiometer 34, the reference mono-wavelength light source 31 is wavelength-scanned with the WBPF 12, specifically, in a state that the filter support plate 11 is kept unmoved at the position corresponding to the scanning step s=25 to capture the two hundred and one mono-wavelength images (hereinafter, also called as "mono-wavelength image group"), integrated values for the respective pixel arrays of the captured mono-wavelength image group are standardized using the reference intensity $M_\lambda$, and relative spectral sensitivities of the mono-wavelength image group are obtained in the range of the pixel array j'=1 to 1,000 on the WBPF 12, which corresponds to 1,000 pixel arrays on the imaging area of the image sensor 7, namely, j=1 to 1,000. Similarly, relative spectral sensitivities in the ranges corresponding to the pixel arrays j'=801 to 1,800 and j'=1,601 to 2,560 on the WBPF 12 are obtained based on the integrated values for the pixel arrays of the wavelength-scanned mono-wavelength image group, with the filter support plate 11 being kept unmoved at the positions corresponding to the scanning step s=45 and 65, respectively. Then, relative spectral sensitivity $S_j(\lambda)$ of the pixel array j'=1 to 2,560 on the entire effective area of the WBPF 12 with 2 nm pitch is obtained based on the relative spectral intensities at the respective positions corresponding to the scanning step s=25, 45, and 65. In the case where relative spectral sensitivities of the pixel array j'=1 to 2,560 on a single entire effective area are generated based on the pixel array ranges at the respective positions corresponding to the scanning step s=25, 45, and 65, namely, based on the pixel arrays j=1 to 1,000, 801 to 1,800, and 1,601 to 2,560, an overlapped area in which the pixel array ranges overlap with each other by about ⅓ pixel array is generated in each of the pixel array ranges. In this case, it is possible to adopt either one of two data obtained from the overlapped area, namely, relative spectral sensitivity information.

Figure 7:
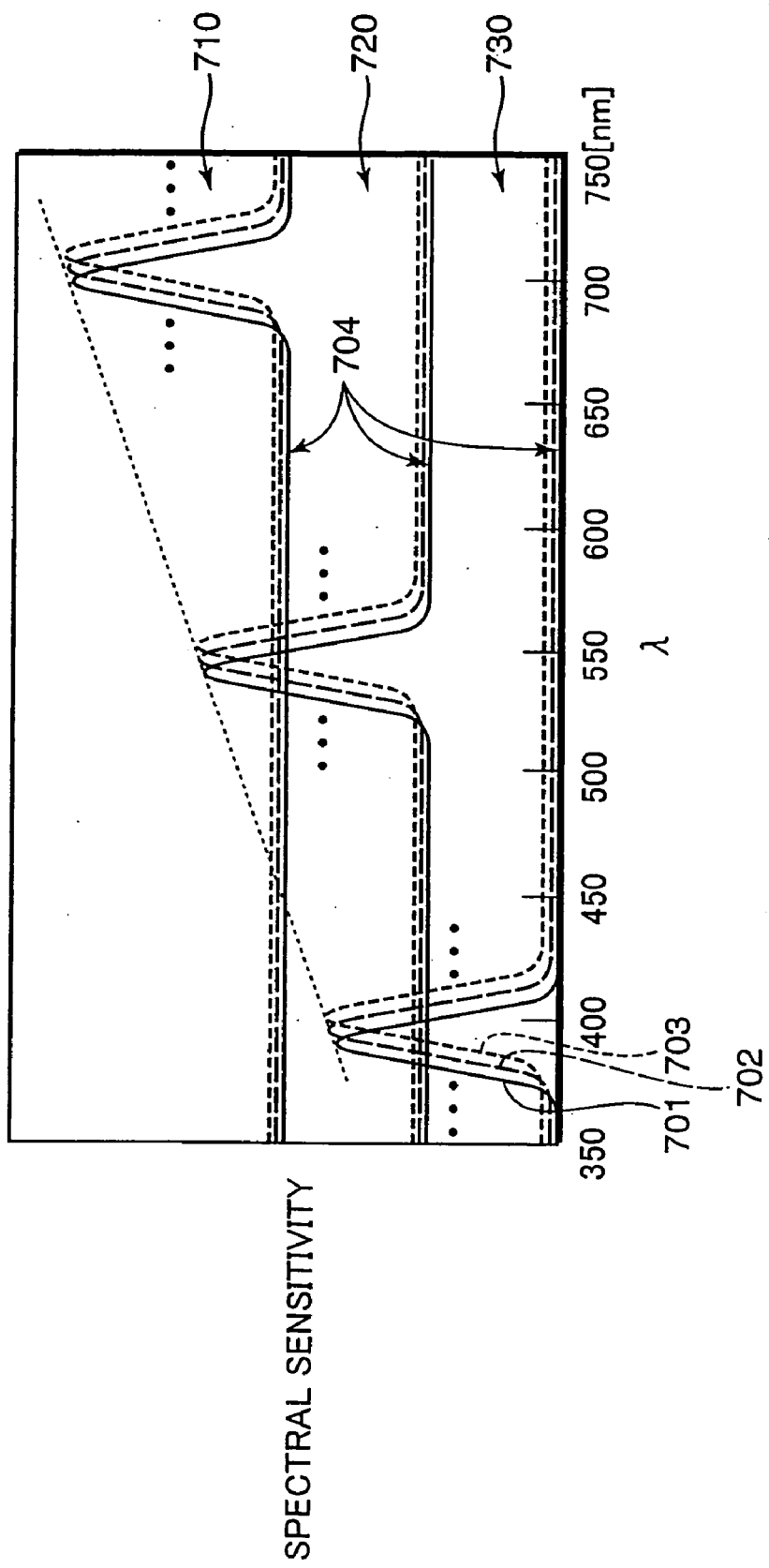
FIG. 7 is a graph showing an example of relative spectral sensitivities of the WBPF in the wavelength axis calibration.

As shown in FIG. 7, the relative spectral sensitivity $s_{sj}(\lambda)$ of each pixel array j on the imaging area of the image sensor 7 at the position corresponding to the scanning step s at the time of measurement is given as the relative spectral sensitivity $S_j(\lambda)$, which is obtained by moving the relative spectral sensitivity $S_j(\lambda)$ of 2,560 pixel arrays on the entire effective area of the WBPF 12 acquired in the above process parallel to the imaging plane of the image sensor 7 depending on the position corresponding to each scanning step s where j'=40·s−j+1. Relative spectral sensitivity waveforms as represented by the reference numerals 701, 702, 703, . . . in FIG. 7 correspond to the respective scanning steps s obtained by the above parallel movement. The interval between the respective relative spectral sensitivity waveforms 701, 702, 703, . . . corresponds to 40 pixels, which is equivalent to one scanning step. Also, axes of abscissas as represented by the reference numeral 704 are identical to each other, and graphs 710, 720, and 730 are expressed at different height positions to clarify the respective spectral sensitivity waveforms in a low wavelength range, a medium wavelength range, and a high wavelength range, wherein the central wavelength varies from 350 nm to 750 nm. It should be noted that since the mono-wavelength image group has the same spectral sensitivity, namely, the same spectral transmittance in a pixel row direction, namely, in the y-direction, an average of the spectral sensitivities of pixel arrays in the pixel row direction is defined as a relative spectral sensitivity of the pixel arrays.

Weighting factors $Wx_{sj}$, $Wy_{sj}$, and $Wz_{sj}$ to be used in the equations (1-1) through (1-3) for the pixel array j at the position corresponding to the scanning step s are obtained as weighting factors $Wx_{sj}$, $Wy_{sj}$, and $Wz_{sj}$ which minimize $Ex_j$, $Ey_j$, and $Ez_j$. $Ex_j$, $Ey_j$, and $Ez_j$ are sums of squares of measurement error in each wavelength and are expressed by the equations (4-1) to (4-3), wherein composite spectral sensitivities $x_j(\lambda)$, $y_j(\lambda)$ and $z_j(\lambda)$ obtained by performing the equations (3-1) to (3-3) and using the relative spectral sensitivity $S_{sj}(\lambda)$, and theoretical figures of color matching functions $x(\lambda)$, $y(\lambda)$, and $z(\lambda)$ are used.

$$x_j(\lambda) = \Sigma_s Wx_{sj} \cdot S_{sj}(\lambda) \quad (3\text{-}1)$$

$$y_j(\lambda) = \Sigma_s Wy_{sj} \cdot S_{sj}(\lambda) \quad (3\text{-}2)$$

$$z_j(\lambda) = \Sigma_s Wz_{sj} \cdot S_{sj}(\lambda) \quad (3\text{-}3)$$

$$Ex_j = \Sigma_\lambda [x_j(\lambda) - x(\lambda)]^2 \quad (4\text{-}1)$$

$$Ey_j = \Sigma_\lambda [y_j(\lambda) - x(\lambda)]^2 \quad (4\text{-}2)$$

$$Ez_j = \Sigma_\lambda [z_j(\lambda) - x(\lambda)]^2 \quad (4\text{-}3)$$

Figure 12:
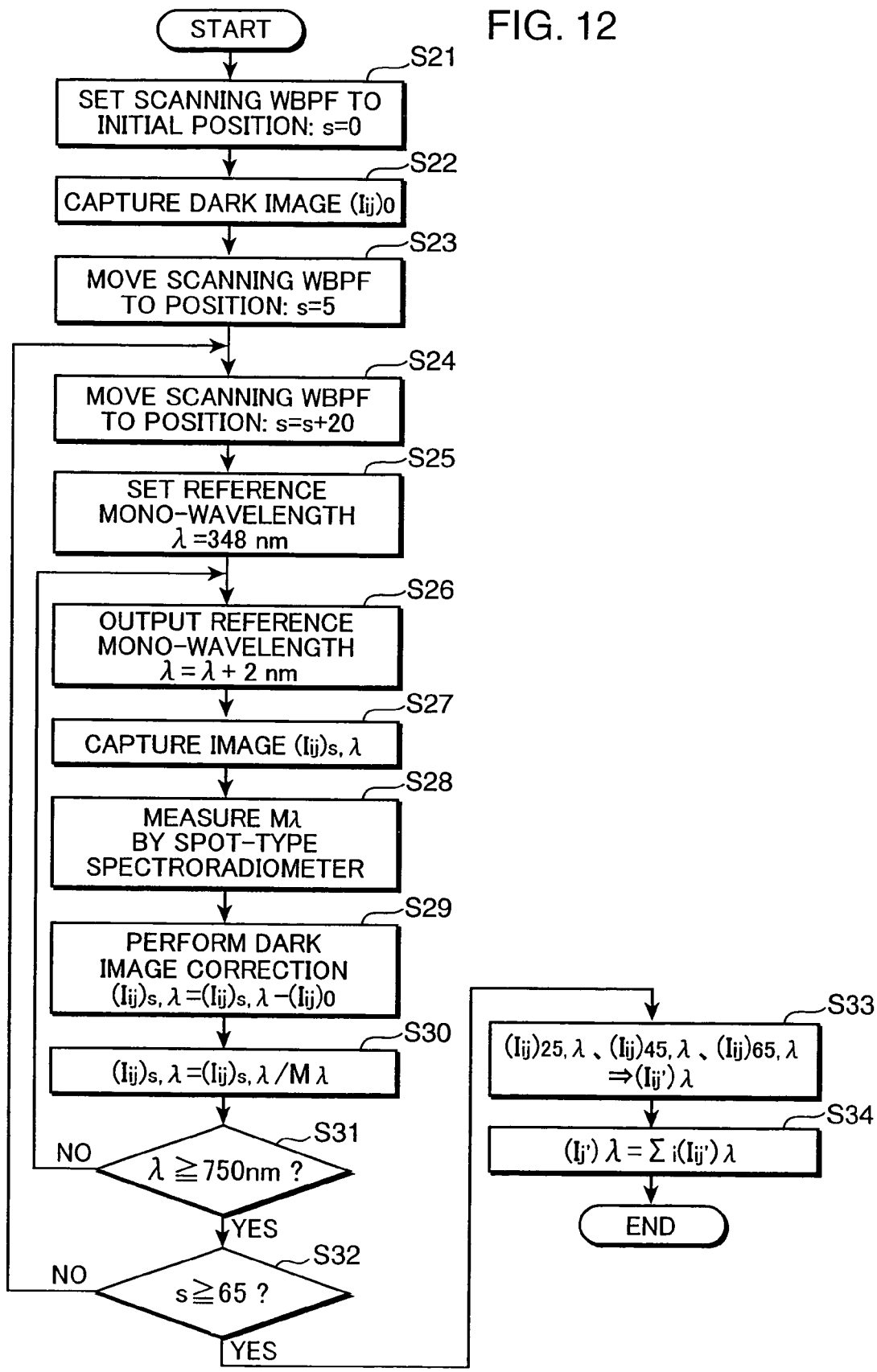
FIG. 12 is a flowchart showing an example of an operation concerning the wavelength axis calibration.

FIG. 12 is a flowchart showing an example of an operation of the wavelength axis calibration. First, the scanning WBPF 10, specifically, the filter support plate 11 of the two-dimensional spectroradiometer 34 for calibration, which is disposed to oppose the uniform luminance surface of the integrating sphere 33, is set to the initial position (s=0) (Step S21), and a dark image $(I_{ij})_0$ is captured in a state that the imaging area of the image sensor 7 is blocked (Step S22). Then, the scanning WBPF 10 is moved to the position corresponding to the scanning step s=25 (Steps S23, S24), and the reference mono-wavelength, namely, the central wavelength λ is set to a predetermined initial value e.g. 348 nm by the reference mono-wavelength light source 31 itself or by the PC 32 (Step S25). Then, a mono-wavelength ray of a central wavelength larger than the central wavelength λ set at the initial position by 2 nm is outputted from the reference mono-wavelength light source 31 (Step S26), and an image $(I_{ij})_{s,\lambda}$ which is formed on the uniform luminance surface of the integrating sphere 33 as a result of emission of the monochromatic ray of the central wavelength λ outputted in Step S26 is captured (Step S27).

On the other hand, the reference intensity $M_\lambda$ is measured by the spot-type reference spectroradiometer 35 (Step S28). The image $(I_{ij})_{s,\lambda}$ captured in Step S27 is corrected using the dark image $(I_{ij})_0$ by implementing the equation: $(I_{ij})_{s,\lambda} = (I_{ij})_{s,\lambda} - (I_{ij})_0$ (Step S29). Then, the correction image $(I_{ij})_{s,\lambda}$ is standardized using the reference intensity $M_\lambda$ obtained in Step S28 by implementing the equation: $(I_{ij})_{s,\lambda} = (I_{ij})_{s,\lambda}/M_\lambda$ for storage (Step S30). If the central wavelength λ of the monochromatic ray outputted from the reference mono-wavelength light source 31 is smaller than 750 nm (NO in Step S31), the routine returns to Step S26, in which an image formed by emission of a monochromatic ray of a central wavelength λ outputted from the reference mono-wavelength light source 31 after increment of 2 nm is captured to perform measurement, namely, detection of the reference intensity $M_\lambda$, the dark image correction, and the standardization. In this way, mono-wavelength rays whose central wavelength is incremented by 2 nm step by step in the wavelength range from 350 nm to 750 nm are successively outputted, and the operations from Steps S27 through S30 for the mono-wavelength rays are cyclically repeated.

If the central wavelength λ of the monochromatic ray outputted from the reference mono-wavelength light source 31 is not smaller than 750 nm (YES in Step S31), and if the scanning step s is smaller than 65 (NO in Step S32), the routine returns to Step S24 to move the scanning WBPF 10, specifically, the filter support plate 11 from the position corresponding to the current scanning step s by twenty scanning steps in the scanning direction i.e. in the plus x-direction, namely, from the position corresponding to the scanning step s=25 in Step S24 to the position corresponding to the scanning step s=45, and to cyclically repeat the operations from Steps S26 through S30 in the wavelength range of the central wavelength λ from 350 nm to 750 nm with 2 nm pitch increment. Likewise, the operations from Steps S26 through S30 are cyclically repeated for the scanning step s=65, which is obtained by moving the filter support plate 11 by twenty scanning steps. As a result of performing the above operations, images $(I_{ij})_{25,\lambda}$, $(I_{ij})_{45,\lambda}$, and $(I_{ij})_{65,\lambda}$ in the respective scanning steps s=25, 45, and 65, which are standardized in Step S30, are obtained for storage.

If the scanning step s is not smaller than 65 (YES in Step S32), namely, after the measurement is completed, the spectral sensitivity image $(I_{ij'})_\lambda$ of the pixel array j'=1 to 2,560 on the entire effective area of the WBPF 12 is obtained based on the stored images $(I_{ij})_{25,\lambda}$, $(I_{ij})_{45,\lambda}$, and $(I_{ij})_{65,\lambda}$ (Step S33). Then, the spectral sensitivity image $(I_{ij'})_\lambda$ is integrated with respect to the pixel row i by implementing the equation: $(I_{j'})_\lambda = \Sigma_i (I_{ij'})_\lambda$. Thus, the spectral sensitivity image $(I_{j'})_\lambda$ with respect to all the pixel arrays j' is obtained for storage (Step S34).

(Luminance Axis Calibration)

Next, the luminance axis calibration is described. What is calibrated by the wavelength axis calibration is the relative spectral sensitivity of each pixel array j at the position corresponding to each scanning step s. Since calibration considering an absolute luminance is not performed, and sensitivity irregularity is not corrected in the wavelength axis calibration, a luminance axis, namely, a sensitivity axis is calibrated. The luminance axis calibration is performed by utilizing the calibration system 30 shown in FIG. 6, for instance. In the luminance axis calibration, light rays emanated from the white light source 36 such as an A light source are allowed to be incident into the integrating sphere 33 to form a uniform luminance surface on the output aperture 332, and the uniform luminance surface is measured by the two-dimensional spectroradiometer 34 for calibration, in place of using the reference mono-wavelength light source 31 as used in the wavelength axis calibration. The uniform luminance surface is simultaneously measured by the reference spectroradiometer 35 to obtain a reference spectral luminance $L_0(\lambda)$.

Then, the sensitivity calibration factor $C_{(ij)s}$ for the pixel $P_{ij}$ at the scanning step s is obtained by implementing the equation (5-1), using the output $\Sigma_\lambda L_0(\lambda) \cdot S_{sj}(\lambda)$, which is supposed to be obtained from the pixel $P_{ij}$ on the pixel array j having the relative spectral sensitivity $S_{sj}(\lambda)$ in the scanning step s when the light source having the reference spectral luminance $L_0(\lambda)$ is measured, and the output $(I_{ij})_s$, which is an actually measured value by the luminance axis calibration.

$$(C_{ij})_s = [\Sigma_\lambda L_0(\lambda) \cdot S_{sj}(\lambda)]/(I_{ij})_s \qquad (5-1)$$

In actually measuring spectral luminance of a two-dimensional light source L by the two-dimensional spectroradiometer 1, the output $(I_{ij})_s$ of the pixel $P_{ij}$ in the scanning step s for measurement of the two-dimensional light source L is converted into a luminance image $(L_{ij})_s$ for output by implementing the equation (6-1).

$$(L_{ij})_s = (C_{ij})_s \cdot (I_{ij})_s \qquad (6-1)$$

(Stray Light Correction)

The WBPF 12 is a multi-layered interference filter, and generally has a characteristic that light components in a wavelength range other than a transmittance wavelength band are reflected thereon. The light components reflected by the WBPF 12 are reflected on a lens surface of an optical system or an inner surface of a housing, and incident onto the WBPF 12 again as stray light. Among the stray light, whereas the light component in the transmittance wavelength band incident on a certain incident site of the WBPF 12 is transmitted through the WBPF 12, and reaches the image sensor 7, the light component that was not transmitted through the WBPF 12 is reflected on the WBPF 12 again as stray light. This process is repeated again and again. In this way, a stray light image composed of the stray light which has reached the image sensor 7 may degrade the precision of an observed image due to superimposing onto an image which is supposed to be observed. In view of this, the following stray light correction is performed to eliminate an influence of the stray light image to the image $(I_{ij})_s$ which has been captured in the respective scanning steps.

The symbols to be used in the description of the stray light correction are described as follows.

m, n: a coordinate of the incident site of light to be measured on the first imaging plane 2b and on the second imaging plane 6b in pixel unit where m, n=1 to 1,000

I, J: a coordinate of a pixel set after binning of 40×40 pixels on the first imaging plane 2b and on the second imaging plane 6b where I, J=1 to 25 M, N: a coordinate of the pixel set on the incident site of light to be measured on the first imaging plane 2b and on the second imaging plane 6b where M, N=1 to 25

Figure 8:
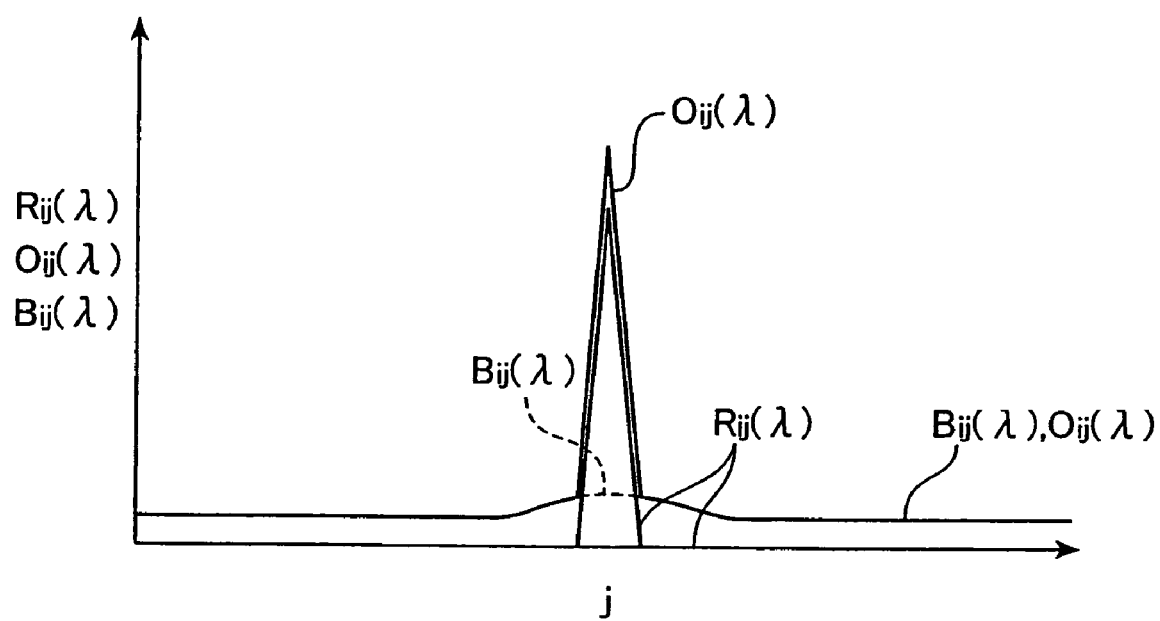
FIG. 8 is a graph showing an example of spectral intensity distributions of a real image $R_{ij}(\lambda)$, an observed image $O_{ij}(\lambda)$, and a stray light image $B_{ij}(\lambda)$.

$R_{ij}(\lambda)$ or $R_{IJ}(\lambda)$: a real image in which a stray light image is not superimposed, namely, an image excluding the stray light $R'_{ij}(\lambda)$ an approximate image to the real image $R_{ij}(\lambda)$ $B_{ij}(\lambda)$ or $B_{IJ}(\lambda)$: a stray light image $O_{ij}(\lambda)$ or $O_{IJ}(\lambda)$: an observed image in which the stray light image is superimposed, namely, an actually measured image expressed by $O_{ij}(\lambda) = R_{ij}(\lambda) + B_{ij}(\lambda)$ or $O_{IJ}(\lambda) = R_{IJ}(\lambda) + B_{IJ}(\lambda)$ $(F_{mn})_{ij}(\lambda)$ or $(F_{MN})_{IJ}(\lambda)$: a response image, namely, an image obtained by an incident ray or rays of a unit intensity which is incident onto the pixel $P_{mn}$ or onto the pixel set $P_{MN}$ $Q_{IJ}(\lambda)$: an estimated correction image used for approximation to the real image $O'_{IJ}(\lambda)$: a pseudo observed image obtained based on the correction image and the response image FIG. 8 shows an example of intensity distributions of the real image $R_{ij}(\lambda)$, the observed image $O_{ij}(\lambda)$, and the stray light image $B_{ij}(\lambda)$. The intensity distributions are expressed along the direction of j-coordinate, namely, in the x-direction. As shown in FIG. 8, the observed image $O_{ij}(\lambda)$ is generated by superimposing the stray light image $B_{ij}(\lambda)$ onto the real image $R_{ij}(\lambda)$. The intensity distribution of the stray light image $B_{ij}(\lambda)$, which does not form an actual image, is flat, namely, substantially constant, with its spatial frequency being exceedingly lower than that of the real image $R_{ij}(\lambda)$, which forms an actual image.

(Response Image)

In this section, the response image is described.

A response image $(F_{mn})_{ij}$ is an image formed when an imaging light ray of a unit intensity incident onto a specific pixel $P_{mn}$ on the measuring area, namely, on the first imaging plane 2b and on the second imaging plane 6b, is incident onto all the pixels $P_{ij}$ on the imaging area of the image sensor 7. The response image $(F_{mn})_{ij}$ can be regarded as a function showing that a point light source for forming an image on the coordinate (m, n) of the incident site includes an influence of the stray light, and showing what influence is given to the entirety of the image as represented by (i,j). The response image $(F_{mn})_{ij}$ is expressed as a function of the wavelength λ: $(F_{mn})_{ij}(\lambda)$ because the level of the stray light which is incident onto a pixel other than the targeted pixel $P_{mn}$, depends (1) on the site where the imaging light ray is incident, namely, the pixel $P_{nm}$ and (2) on the site where the stray light is incident, namely, the pixel $P_{ij}$, and (3) on the wavelength of the imaging light ray. The reason (3) is given because reflection and transmittance associated with the stray light generally have dependency on wavelength.

Defining the response image as mentioned above, the observed image $O_{ij}(\lambda)$ which is actually measured or observed by the two-dimensional spectroradiometer 1 can be obtained by implementing the equation (7-1), namely, by integrating the response image $(F_{mn})_{ij}(\lambda)$ with respect to all the incident pixels $P_{mn}$, in which the response image $(F_{mn})_{ij}(\lambda)$ is weighted by the real image $R_{mn}(\lambda)$ having an intensity of a ray to be incident onto the incident pixel $P_{mn}$.

$$O_{ij}(\lambda)=\Sigma_{mn}[R_{mn}(\lambda)\cdot(F_{mn})_{ij}(\lambda)] \tag{7-1}$$

(Estimation of Real Image)

In stray light correction, the real image $R_{ij}(\lambda)$ is obtained by removing an influence of stray light from the observed image $O_{ij}(\lambda)$. In this section, description is made regarding how the real image $R_{ij}(\lambda)$ is estimated based on the observed image $O_{ij}(\lambda)$.

A correction image which is approximate to the real image $R_{ij}(\lambda)$ excluding the influence of a stray light image is obtained as the estimated real image $R_{ij}(\lambda)$ by implementing the equation (7-1) using the observed image $O_{ij}(\lambda)$ and the response image $(F_{mn})_{ij}(\lambda)$ First, an initial value $R_{ij}(\lambda)^{(0)}$ of a correction image which is approximate to the real image $R_{ij}(\lambda)$ is defined as $O_{mn}(\lambda)$, namely, $R_{ij}(\lambda)^{(0)}=O_{mn}(\lambda)$ Then, a first order correction image $R_{ij}(\lambda)^{(1)}$, which is a first order approximate solution, is obtained by correcting the initial value $R_{ij}(\lambda)^{(0)}$ using $\Sigma_{mn}[R_{ij}(\lambda)^{(0)}\cdot(F_{nm})_{ij}(\lambda)]-O_{ij}(\lambda)$, which is a difference between a pseudo observed image $\Sigma_{mn}[R_{ij}(\lambda)^{(0)}\cdot(F_{nm})_{ij}(\lambda)]$ calculated based on the initial value $R_{ij}(\lambda)^{(0)}$ and the response image $(F_{mn})_{ij}(\lambda)$, and the actually observed image $O_{ij}(\lambda)$, namely by implementing the equation (8-1).

$$R_{ij}(\lambda)^{(1)}=R_{ij}(\lambda)^{(0)}-a\cdot[\Sigma_{mn}[R_{ij}(\lambda)^{(0)}\cdot(F_{mn})_{ij}(\lambda)]-O_{ij}(\lambda)] \tag{8-1}$$

Further, a second order correction image $R_{ij}(\lambda)^{(2)}$ is obtained by implementing the equation (9-1), namely, by substituting $R_{ij}(\lambda)^{(1)}$ for the right-side term $R_{ij}(\lambda)^{(0)}$ in the equation (8-1).

$$R_{ij}(\lambda)^{(2)}=R_{ij}(\lambda)^{(1)}-a\cdot[\Sigma_{mn}[R_{ij}(\lambda)^{(1)}\cdot(F_{mn})_{ij}(\lambda)]-O_{ij}(\lambda)] \tag{9-1}$$

The above computation is repeated for a certain number of times by implementing the following equation (10-1) using $R_{mn}(\lambda)^{(k-1)}$ to yield a correction image $R_{ij}(\lambda)^{(k)}$ of k-order.

$$R_{ij}(\lambda)^{(k)}=R_{ij}(\lambda)^{(k-1)}-a\cdot[\Sigma_{mn}[R_{ij}(\lambda)^{(k-1)}\cdot(F_{mn})_{ij}(\lambda)]-O_{ij}(\lambda)] \tag{10-1}$$

The symbol "a" affixed to the second term of the right side in the equation (8-1), (9-1), (10-1) is a constant to give asymptotic characteristic, and is empirically selected so that the asymptotic equation is converged. By implementing the above processes, the k-order correction image $R_{ij}(\lambda)^{(k)}$, which is obtained for the first time, and which makes the sum of square (see the equation (11-1)) in the second term on the right side of the equation (8-1), (9-1), (10-1) which is a correction term, for each pixel, equal to or smaller than an allowable value, is defined as an approximate image $R'_{ij}(\lambda)$. The k-order correction image $R_{ij}(\lambda)^{(k)}$, namely, the approximate image $R'_{ij}(\lambda)$ represents a correction image used for approximation to the real image $R_{ij}(\lambda)$, namely, an estimated real image $R_{ij}(\lambda)$.

$$E^{(k-1)}=\Sigma_{ij}[\Sigma_{mn}[R_{ij}(\lambda)^{(k-1)}\cdot(F_{mn})_{ij}(\lambda)]-O_{ij}(\lambda)]^2 \tag{11-1}$$

The stray light image is obtained as $B_{ij}(\lambda)$ in the following equation (12-1) using the k-order correction image $R_{ij}(\lambda)^{(k)}$. In other words, the stray light image $B_{ij}(\lambda)$ is obtained by subtracting the estimated real image $R_{ij(\lambda)}^{(k)}$ from the observed image $O_{ij}(\lambda)$.

$$B_{ij}(\lambda)=O_{ij}(\lambda)-R_{ij}(\lambda)^{(k)} \tag{12-1}$$

(Actual Computation)

When the above computation is performed with respect to pixels of $10^6$ of the image sensor 7, data of $10^{12}$ is necessary for the first order computation, which requires an enormous amount of data and time for computation. In view of this, a technique is used, in which a stray light image is obtained, and an approximate image $R'_{ij}(\lambda)$ is obtained by implementing the equation (13-1), which is a modified equation of the equation (12-1), namely, by subtracting a stray light image $G_{ij}(\lambda)$ corresponding to the stray light image $B_{ij}(\lambda)$ from the observed image $O_{ij}(\lambda)$.

$$R'_{ij}(\lambda)^{(k)}=O_{ij}(\lambda)-G_{ij}(\lambda) \tag{13-1}$$

The reason for using the above technique is that the stray light does not include a high spatial frequency component, has sufficient precision even in image information of a low pixel number, and that the amount of image information and the computation time can be remarkably reduced by reducing the pixel number, namely, by using image information of a low pixel number, as described referring to FIG. 8. Also, it is possible to secure sufficient precision by an approximate image, namely, a correction image approximate to a real image, wherein the approximate image is obtained by converting a stray light image of a low pixel number into a stray light image of the original pixel number, namely, having all the pixels on the imaging area of the image sensor 7 by implementing a well-known process such as smoothing, and by subtracting the stray light image of the original pixel number from the observed image having all the pixels.

Figure 9:
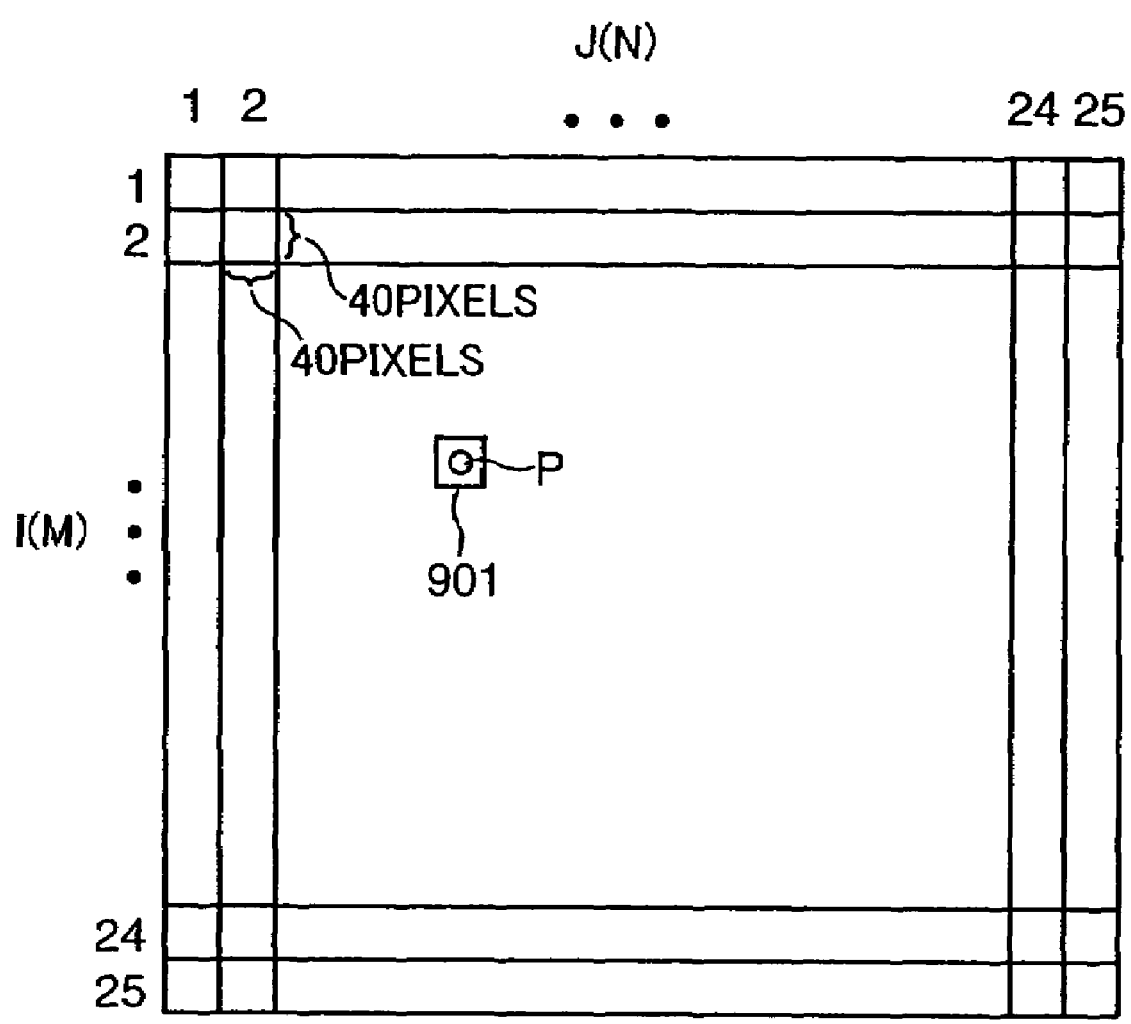
FIG. 9 is a conceptual illustration for describing a pixel set coordinate of an image obtained by binning.

In view of the above, in this embodiment, as shown in FIG. 9, a stray light image is obtained by binning 40×40 pixels for integration, using image information relating to 25×25 pixel sets (=I×J and M×N). Specifically, the pixel coordinates (i,j) and (m,n) where i,j, m,n=1 to 1,000 are replaced with the pixel set coordinates (I,J) and (M,N) where I,J,M,N=1 to 25, and as the pixel coordinate replacement is performed, the observed image $O^{ij}(\lambda)$, the real image $R^{ij}(\lambda)$, the response image $(F_{mn})_{ij}(\lambda)$, and the stray light image $B_{ij}(\lambda)$ are replaced with $O_{IJ}(\lambda)$, $R_{IJ}(\lambda)$, $(F_{MN})_{IJ}(\lambda)$, and $B_{IJ}(\lambda)$, which are obtained by binning of 40×40 pixels. It is possible to reduce the image information amount to e.g. $10^{-4}/256$, and shorten the computation time accordingly by handling the binned information in each of the computations so that the above technique is practically used.

(Actual Measurement of Response Image)

In the computation for spectral luminance measurement by the two-dimensional spectroradiometer 1, as mentioned above, the correction image approximate to the real image $R_{ij}(\lambda)$ excluding the influence of the stray light image, namely, the estimated real image $R_{ij}(\lambda)$ is obtained based on the observed image $O_{ij}(\lambda)$ and the response image $(F_{mn})_{ij}(\lambda)$. The information relating to the response image used in this computation is obtained in advance e.g. before shipment by actual measurement. In the following, actual measurement of the response image is described.

Figure 10B:
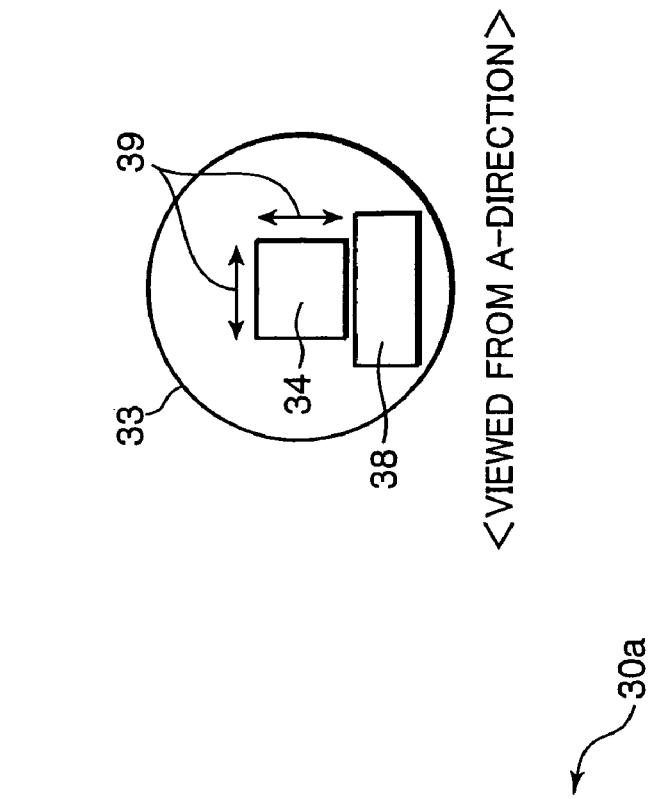
FIG. 10B is an illustration viewed from the direction of the arrow A in FIG. 10A.
Figure 10A:
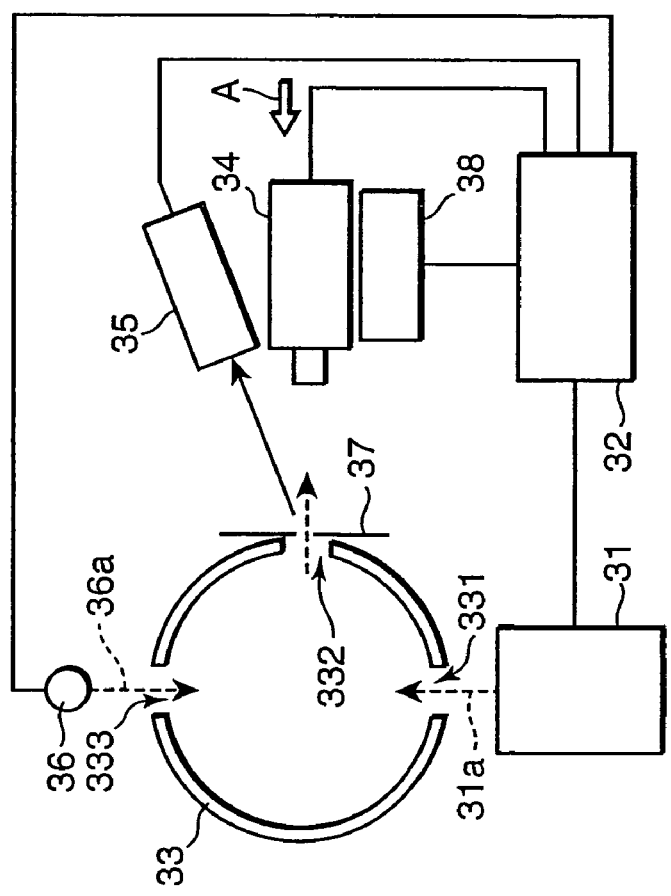
FIG. 10A is a schematic illustration showing an example of a calibration system to be used in actual measurement of a response image.

The actual measurement of the response image is performed using a calibration system 30a shown in FIG. 10A, for instance. The calibration system 30a is additionally provided with a pin-hole plate 37 and a movable table 38 in addition to components corresponding to the components of the calibration system 30 shown in FIG. 6. As shown in FIG. 10A, in actual measurement of the response image, first, white rays 36a emanated from a white light source 36 are incident onto an integrating sphere 33, and a point light source is formed by disposing the pin-hole plate 37 near an output aperture 332 of the integrating sphere 33. The white ray from the point light source is measured by a two-dimensional spectroradiometer 34 for calibration, which is placed on the movable table 38. The movable table 38 is movable in the x-direction and in the y-direction, namely, in the directions shown by the arrows 39 in FIG. 10B, which is an illustration viewed from the direction of the arrow A in FIG. 10A. By controllably moving the movable table 38 by a personal computer (PC) 32 designed for controlling, the two-dimensional spectroradiometer 34 can be moved to such a position that an image of the point light source is incident onto an arbitrary coordinate on the first imaging plane 2b and on the second imaging plane 6b, namely, onto the pixel set coordinate (M,N) where M=1 to 25, N=1 to 25 (see the point light source P on the pixel set 901 shown in FIG. 9, for instance). The spectral intensity of the white ray emanated through the pin-hole of the pin-hole plate 37 is measured by the reference spectroradiometer 35 to obtain a relative spectral intensity M(λ) based on a monitor output by the measurement.

Figure 13:
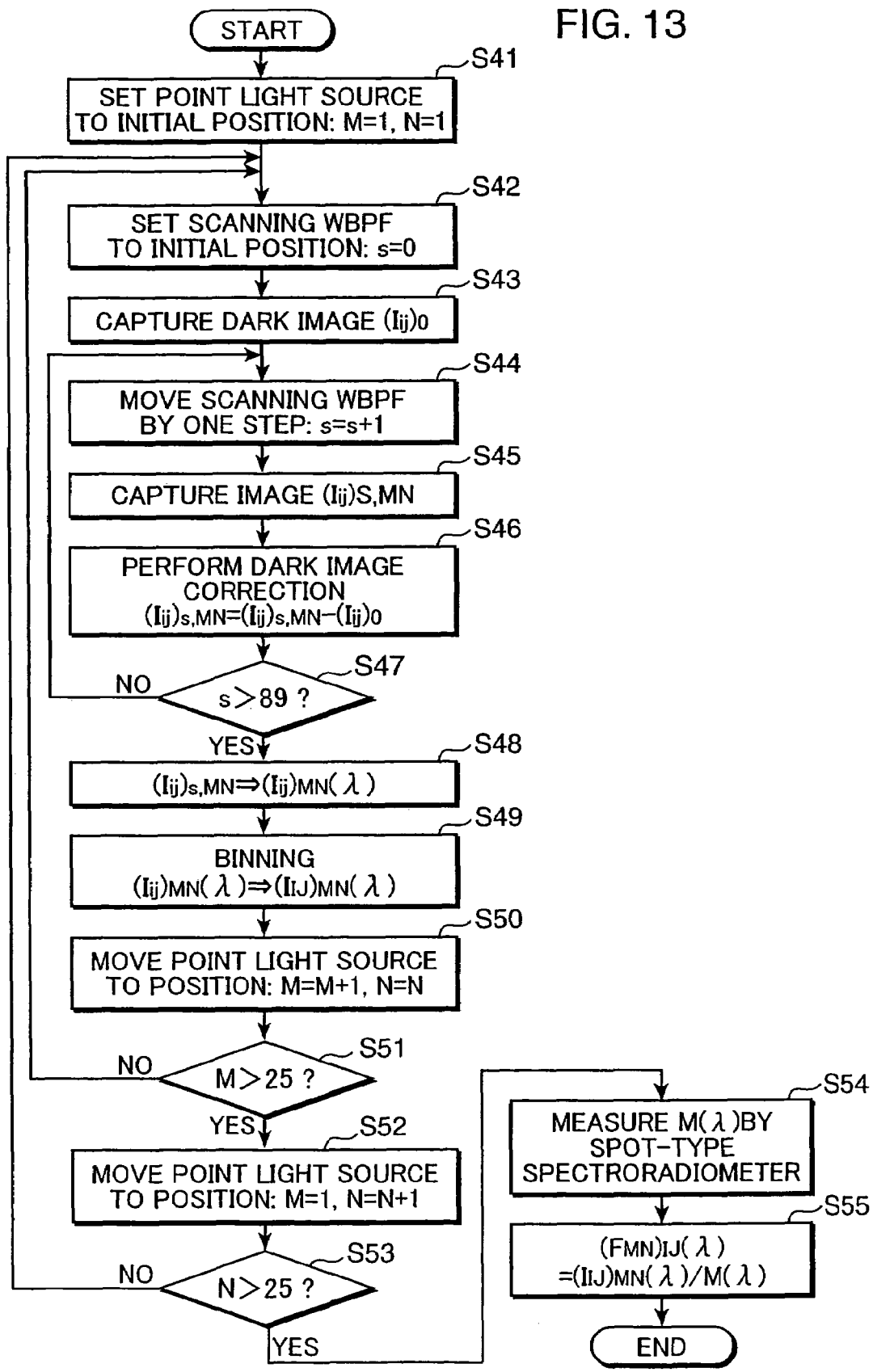
FIG. 13 is a flowchart showing an example of an operation concerning the actual measurement of a response image.

FIG. 13 is a flowchart showing an example of an operation of the actual measurement of the response image. First, the position of the movable table 38 is controllably moved by the PC 32 to set the point light source to an initial position, namely, to set the pixel set coordinate (M,N) on the first imaging plane 2b or on the second imaging plane 6b to the position of M=1, N=1, for instance (Step S41). When the point light source is located at the pixel set coordinate position, the filter support plate 11, specifically, the WBPF 12 is set to the initial position corresponding to the scanning step s=0 by the scanning driver 13 of the scanning WBPF 10 (Step S42). At the scanning step s=0, a dark image $(I_{ij})_0$ is captured by the image sensor 7, and is outputted to the main controller 9 via the image signal processor 8 (Step S43). Subsequently, the scanning step s is incremented by one (Step S44), and, similarly to the operation in Step S43, an image $(I_{ij})_{S,MN}$ is captured by the image sensor 7 for outputting to the main controller 9 (Step S45). The image $(I_{ij})_{S,MN}$ undergoes dark image correction for storage: $(I_{ij})_{S,MN}=(I_{ij})_{S,MN}-(I_{ij})_0$ (Step S46).

If the scanning step s is not larger than 89 (NO in Step S47), the routine returns to Step S44 where the filter support plate 11 is moved to a next scanning step s, and operations of capturing the image $(I_{ij})_{S,MN}$, and performing dark image correction for storage are repeated each time the scanning step is performed (Steps S45, S46). If the scanning step s is larger than 89 (YES in Step S47), the stored image $(I_{ij})_{S,MN}$ after the dark image correction is converted into a spectral intensity image $(I_{ij})_{MN}(\lambda)$ (Step S48). Then, the spectral intensity image $(I_{ij})_{MN}(\lambda)$ is converted into a spectral intensity image $(I_{IJ})_{MN}(\lambda)$ at the pixel set coordinate (I,J), in which the data number is reduced by binning of 40×40 pixels, for storage (Step S49).

Subsequently, the M-coordinate of the point light source is incremented by one, namely, M=M+1, N=N (Step S50). If the M-coordinate value is not larger than 25 (NO in Step S51), the routine returns to Step S42 while keeping the pixel set coordinate position unchanged, and the filter support plate 11, specifically, the WBPF 12 is set to the initial position corresponding to the scanning step s=0, and similarly to the operation in Steps S45, S46, and S49, image capturing, dark image correction, and binning are performed. If the M-coordinate value is larger than 25 (YES in Step S51), the M-coordinate of the point light source is set to one, and the N-coordinate of the point light source is incremented by one, namely, M=1, N=N+1 (Step S52). If the N-coordinate value is not larger than 25 (NO in Step S53), the routine returns to Step S42 while keeping the pixel set coordinate position unchanged, and the operations from Steps S43 through S52 are cyclically repeated. In this way, the pixel set coordinate (M,N) is successively moved from the initial position (1,1) to (25, 25), and the operations from Steps S42 through S49 are cyclically repeated while keeping the respective corresponding coordinate positions unchanged. If the N-coordinate value is larger than 25, and if the spectral intensity image $(I_{IJ})_{MN}(\lambda)$, which represents incidence of the point light source onto all the pixel set coordinates (M,N), is obtained (YES in Step S53), the relative spectral intensity M(λ) of the point light source is measured by the spot-type reference spectroradiometer 35 (Step S54). Then, the spectral intensity image $(I_{IJ})_{MN}(\lambda)$ is standardized by the relative spectral intensity M(λ) for each wavelength: $F(_{MN})_{IJ}(\lambda)=(I_{IJ})_{MN}(\lambda)/M(\lambda)$ to be stored as a response image $(F_{MN})_{IJ}(\lambda)$ (Step S55). Then, the flow ends.

(Stray Light Correction in Measurement)

In this section, description is made as to an example of computation in the case where stray light correction is performed at the time of measurement by the two-dimensional spectroradiometer 1. In the foregoing section described referring to the flowchart shown in FIG. 11, stray light correction is not performed. However, in this section, stray light correction is performed. In the case where stray light correction is performed at the time of measurement, first, an optical image of the two-dimensional light source L is captured each time the scanning step s is performed by the scanning WBPF 10, specifically, by the WBFP 12, and an image $(I_{ij})_s$ after dark image correction: $(I_{ij})_s=(I_{ij})_s-(I_{ij})_0$ is stored as an observed image $(O_{ij})_s$. After the scanning is completed, the observed image $(O_{ij})_s$ is converted into an observed image $O_{ij}(\lambda)$, which is a spectral image as a function of the wavelength λ, and the observed image $O_{ij}(\lambda)$ is converted into an observed image $O_{IJ}(\lambda)$ composed of the pixel set (I,J) obtained by binning of 40×40 pixels. Then, the binned observed image $O_{IJ}(\lambda)$ is presumably obtained as a correction image $Q_{IJ}(\lambda)$, and a pseudo observed image $O'_{IJ}(\lambda)$ is obtained by implementing the equation (14-1), which is a modified equation of the equation (7-1), using $Q_{MN}(\lambda)$ corresponding to the correction image $Q_{IJ}(\lambda)$, and the actually measured and stored response image $(F_{MN})_{IJ}(\lambda)$, wherein $Q_{MN}(\lambda)$ represents the intensity of rays to be incident onto the pixel set at the M,N-coordinate.

$$O'_{IJ}(\lambda)=\Sigma_{MN}[Q_{MN}(\lambda)\cdot(F_{MN})_{IJ}(\lambda)] \tag{14-1}$$

Next, as expressed by the equation (15-1), the correction image $Q_{IJ}(\lambda)$ is re-corrected using a difference between the pseudo observed image $O'_{IJ}(\lambda)$ and the observed image $O_{IJ}(\lambda)$: $[O'_{IJ}(\lambda)-O_{IJ}(\lambda)]$, and the re-corrected image is defined as a correction image $Q_{IJ}(\lambda)$.

$$Q_{IJ}(\lambda)=Q_{IJ}(\lambda)-a\cdot[O'_{IJ}(\lambda)-O_{IJ}(\lambda)] \tag{15-1}$$

Then, as expressed by the equation (16-1), the correction image $Q_{IJ}(\lambda)$, which is obtained for the first time, and which makes a square sum E(λ) of the difference between the pseudo observed image $O'_{IJ}(\lambda)$ and the observed image $O_{IJ}(\lambda)$ for each pixel smaller than a predetermined limit value Et, is defined as a final correction image.

$$E(\lambda)=\Sigma_{IJ}[O'_{IJ}(\lambda)-O_{IJ}(\lambda)]^2 \tag{16-1}$$

In the case where E(λ) is not smaller than the limit value Et, the computations (14-1), (15-1), and (16-1) are cyclically repeated until E(λ) is smaller than the limit value Et.

When the final correction image $Q_{IJ}(\lambda)$ is obtained, a stray light image $B_{IJ}(\lambda)$ is obtained by implementing the equation (17-1), namely, by subtracting the final correction image $Q_{IJ}(\lambda)$ from the observed image $O_{IJ}(\lambda)$.

$$B_{IJ}(\lambda)=O_{IJ}(\lambda)-Q_{IJ}(\lambda) \tag{17-1}$$

The stray light image $B_{IJ}(\lambda)$ is a stray light image composed of a pixel set obtained by the binning. Accordingly, the stray light image $B_{IJ}(\lambda)$ is converted into a stray light image $B_{ij}(\lambda)$ composed of all the pixels before the binning by performing a smoothing process. As mentioned above, since the stray light image has a low spatial frequency, there is no significant measurement error between the stray light image $B_{ij}(\lambda)$ after the smoothing of the stray light image $B_{IJ}(\lambda)$, and the stray light image $B_{ij}(\lambda)$ composed of all the pixels, which is obtained by implementing the equation (12-1). Accordingly, an approximate image $R'_{ij}(\lambda)$ is obtained by subtracting the stray light image $B_{ij}(\lambda)$ from the observed image $O_{ij}(\lambda)$, namely, by implementing the equation (18-1).

$$R'_{ij}(\lambda)=O_{ij}(\lambda)-B_{ij}(\lambda) \quad (18\text{-}1)$$

In this way, stray light correction is performed by obtaining the stray light image $B_{ij}(\lambda)$ by performing the computation using the image $(I_{ij})_s$, which is captured each time the two-dimensional light source L is scanned in the scanning step s, namely, using the observed image $O_{ij}(\lambda)$ and the pre-stored response image $(F_{MN})_{IJ}(\lambda)$, and by subtracting the stray light image $B_{ij}(\lambda)$ from the observed image $O_{ij}(\lambda)$. Thus, the approximate image $R'_{ij}(\lambda)$ is obtained.

A spectral luminance image $L_{ij}(\lambda)$, which will be described later, can be obtained, by applying the aforementioned luminance correction to the approximate image $R'_{ij}(\lambda)$. It is necessary to acquire a calibration factor to be used in the luminance correction in advance by performing a luminance axis calibration similar to the aforementioned luminance axis calibration. Specifically, an image of the uniform luminance surface to be formed by emission of rays from the white light source 36 in FIG. 6 is acquired by measurement, and an approximate image $R'_{ij}(\lambda)$ similar to the approximate image $R'_{ij}(\lambda)$ is obtained by applying the stray light correction to the acquired image by implementing equations similar to the equations (14-1), (15-1), (16-1), (17-1), and (18-1). Concurrently, an image of the uniform luminance surface is measured by the spot-type reference spectroradiometer 35 to obtain a reference spectral luminance $L_0(\lambda)$. Then, as expressed by the equation (19-1), a calibration factor $C_{ij}(\lambda)$ as a function of the wavelength λ is obtained, using the approximate image $R'_{ij}(\lambda)$ and the reference spectral luminance $L_0(\lambda)$ for storage in the main controller 9 or the like.

$$C_{ij}(\lambda)=L_0(\lambda)/R'_{ij}(\lambda) \quad (19\text{-}1)$$

At the time of actual measurement by the two-dimensional spectroradiometer 1, the image of the two-dimensional light source L acquired by the measurement undergoes the stray light correction by implementing the equations (14-1), (15-1), (16-1), (17-1), and (18-1) to obtain an approximate image $R'_{ij}(\lambda)$, and the approximate image $R'_{ij}(\lambda)$ is converted into a spectral luminance image $L_{ij}(\lambda)$ for output using the stored calibration factor $C_{ij}(\lambda)$, namely, by implementing the equation (20-1).

$$L_{ij}(\lambda)=C_{ij}(\lambda) \cdot R'_{ij}(\lambda) \quad (20\text{-}1)$$

Figure 14:
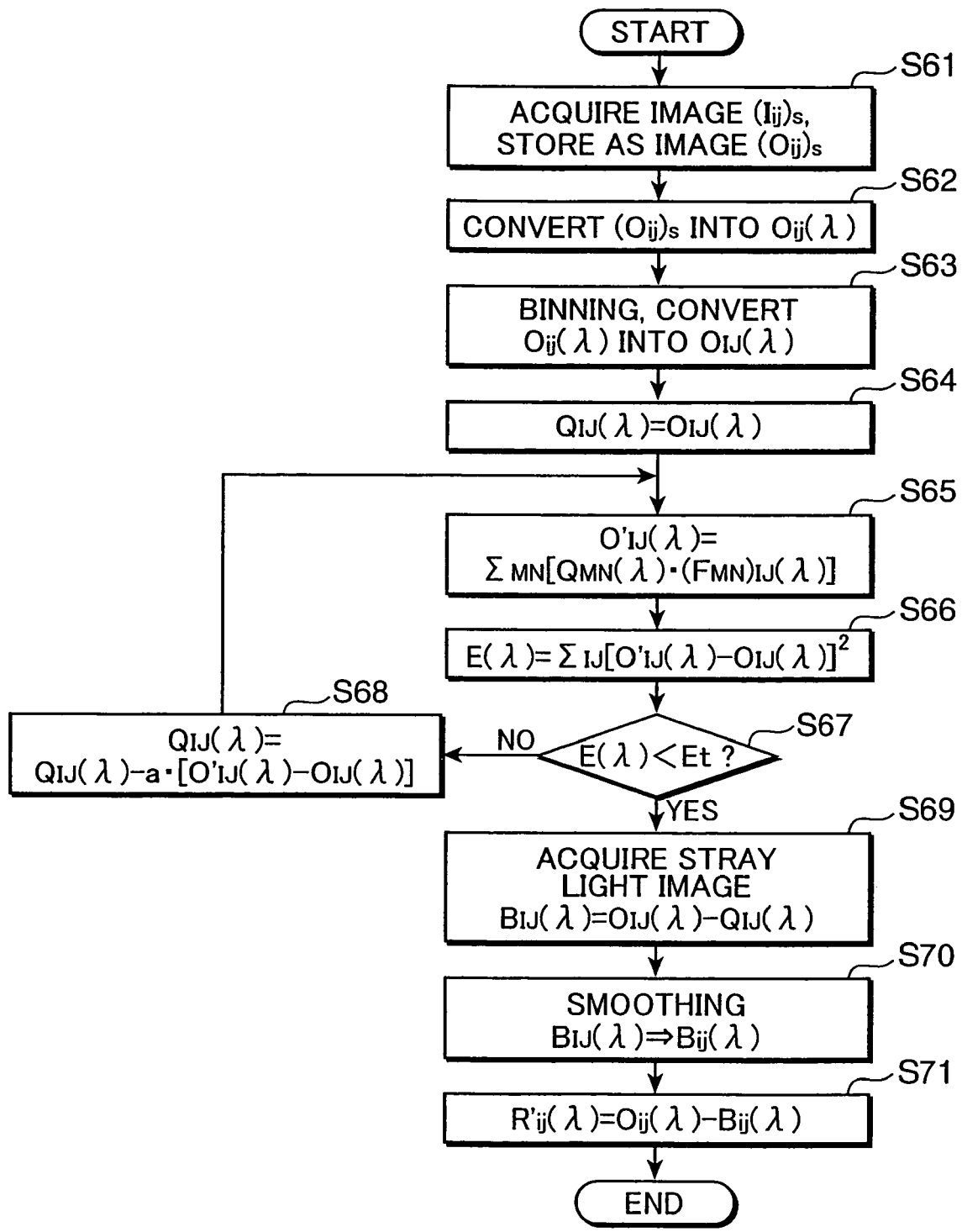
FIG. 14 is a flowchart showing an example of an operation concerning stray light correction in measurement by the two-dimensional spectroradiometer.

FIG. 14 is a flowchart showing an example of an operation of the stray light correction to be implemented at the time of measurement by the two-dimensional spectroradiometer 1. First, an image $(I_{ij})_s$, which is captured each time the scanning step s is performed by the scanning WBPF 10, specifically, by the WBPF 12, and which undergoes dark image correction: $(I_{ij})_s=(I_{ij})_s-(I_{ij})_0$, is stored as an observed image $(O_{ij})_s$ (Step S61). The observed image $(O_{ij})_s$ is converted into an observed image $O_{ij}(\lambda)$ (Step S62). Next, the observed image $O_{ij}(\lambda)$ is converted into an observed image $O_{IJ}(\lambda)$ composed of the pixel set obtained by binning of 40×40 pixels (Step S63). Then, the observed image $O_{IJ}(\lambda)$ is set as a correction image $Q_{IJ}(\lambda)$ (Step S64), and a pseudo observed image $O'_{IJ}(\lambda)$ is obtained by implementing the equation (14-1), using $Q_{MN}(\lambda)$ corresponding to the correction image $Q_{IJ}(\lambda)$, and the response image $(F_{MN})_{IJ}(\lambda)$ (Step S65).

Subsequently, as expressed by the equation (16-1), a square sum $E(\lambda)$ of the difference between the pseudo observed image $O'_{IJ}(\lambda)$ and the observed image $O_{IJ}(\lambda)$ for each pixel is obtained (Step S66). If the value of $E(\lambda)$ is not smaller than the predetermined limit value Et (NO in Step S67), the correction image $Q_{IJ}(\lambda)$ is re-corrected by using the difference between the pseudo observed image $O'_{IJ}(\lambda)$ and the observed image $O_{IJ}(\lambda)$: $O'_{IJ}(\lambda)-O_{IJ}(\lambda)$, and the re-corrected image is set as a correction image $Q_{IJ}(\lambda)$ (Step S68). Then, the routine returns to Step S65 to repeat the computations from Steps S65 through S68 until the value of $E(\lambda)$ is smaller than the limit value Et. If the value of $E(\lambda)$ is smaller than the limit value Et (YES in Step S67), the correction image $Q_{IJ}(\lambda)$, which is obtained for the first time when the value of $E(\lambda)$ is smaller than the limit value Et, is determined as the final correction image, and as expressed by the equation (17-1), a stray light image $B_{IJ}(\lambda)$ is obtained by subtracting the correction image $Q_{IJ}(\lambda)$ from the observed image $O_{IJ}(\lambda)$ (Step S69). Thereafter, the stray light image $B_{IJ}(\lambda)$ undergoes a smoothing process, and is converted into a stray light image $B_{ij}(\lambda)$ composed of all the pixels (Step S70). Then, as expressed by the equation (18-1), an approximate image $R'_{ij}(\lambda)$ is obtained by subtracting the stray light image $B_{ij}(\lambda)$ from the observed image $O_{ij}(\lambda)$ (Step S71).

As mentioned above, according to the two-dimensional spectroradiometer 1 in the embodiment, light rays La from the two-dimensional light source L for measurement are captured by the optical system including the objective optical system 2, the first condenser lens 4, the second condenser lens 5, and the relay lens 6 to form the optical image, namely, the first image 2a and the second image 6a. The WBPF 12, which is a transmittance wavelength variable filter, has a spectral transmittance characteristic that transmittance wavelengths of the light rays La differ depending on the transmittance sites of the respective light rays La. The scanning WBPF 12 is scannably held by the scanning WBPF 10 on the optical path of the first imaging plane 2b, namely, on the light rays La. Also, the optical image, namely, the second image 6a composed of the light rays La passing through the WBPF 12 at the position corresponding to each of the scanning steps s is captured by the image sensor 7 to obtain the plural images $(I_{ij})_s$ or the images $(O_{ij})_s$ whose spectral sensitivity differs among the pixels each time the scanning step s is performed at the respective corresponding positions.

In this way, plural images each having a different spectral sensitivity among the pixels is obtained each time the scanning step s is performed at the respective corresponding positions. Specifically, the pixels of the image $(I_{ij})_s$ captured by the image sensor 7 at the position corresponding to each of the scanning steps s are composed of light rays La having a different spectral characteristic depending on the transmittance sites of the respective light rays La, in place of being composed of light rays having the same transmittance wavelength i.e. monochromatic rays of the same central wavelength λ namely, having the same spectral characteristic. This enables to obtain spectral characteristic information relating to a wavelength range necessary for each pixel by successively moving the single WBPF 12 for scanning in each scanning step. In other words, plural images each having spectral sensitivity information, in which the spectral sensitivity differs among the pixels, can be obtained by using the single WBPF 12. This arrangement enables to remarkably reduce the number of filters necessary for scanning, which resultantly reduces a load concerning scan driving of the scanning WBPF 10, or the moving distance, namely, the scanning distance in scanning. This arrangement contributes to remarkable size reduction of the two-dimensional spectroradiometer as a whole, and production cost reduction thereof, and enables to shorten the measurement time, and consequently realizes a handy two-dimensional spectroradiometer of high operability.

Also, scanning is performed by the scanning WBPF 10 in such a manner that the WBPF 12 is moved in one direction, in this embodiment, in the x-direction on the first imaging plane 2b or on the second imaging plane 6b relative to the light rays La forming the optical path, namely, the optical image. This arrangement enables to acquire plural images each having a different spectral sensitivity among the pixels with use of the WBPF 12 with a simplified arrangement that the WBPF 12 is moved in one direction on the first imaging plane 2b. This contributes to further shortening of the scanning time, namely, the measurement time.

Further, the WBPF 12 is arranged near the first imaging plane 2b for forming the first image 2a by the objective optical system 2, and the image sensor 7 is arranged on the second imaging plane 6b for forming the second image 6a by the relay optical system comprised of the second condenser lens 5 and the relay lens 6. This arrangement allows to dispose the WBPF 12 away from the image sensor 7, to suppress stray light due to plane reflection between the WBPF 12 and the image sensor 7, and to construct the image sensor 7 easily without a possibility of interference with the WBPF 12. If the WBPF 12 is not disposed away from the image sensor 7, it is necessary to position the WBPF 12 relative to the image sensor 7 with high precision in a state that the WBPF 12 is located close to the image sensor 7, namely, in front of the image sensor 7.

Furthermore, the light blocking portion for blocking light from the imaging area T of the second image 6a on the second imaging plane 6b corresponding to the image sensor 7 is formed on both or one of the side portions of the filter support plate 11 in the scanning direction of the WBPF 12. This arrangement enables to move the transmittance wavelength variable filter by the scanner for scanning, and at the same time to acquire information relating to each pixel, as a dark image $(I_{ij})_0$. The pixel information is obtained by blocking the imaging area T with the light blocking portion formed on the transmittance wavelength variable filter, which, in this embodiment, corresponds to the first light blocking portion 112 and the second light blocking portion 113 formed on the left and right sides of the filter support plate 11. This arrangement enables to simplify the construction of the two-dimensional spectroradiometer without the need of additionally providing a light blocker for performing dark image correction and a scanner for moving the light blocker for scanning.

The WBPF 12 is a wedge band pass filter having a characteristic that a central wavelength of the light rays La passing through the respective transmittance sites of the WBPF 12 is sequentially varied in the scanning direction of the WBPF 12, namely, in the x-direction. This arrangement enables to obtain plural images each having a different spectral sensitivity among the pixels with a simplified arrangement of causing the wedge band pass filter to move in the scanning direction.

Further, the image $(I_{ij})_s$ obtained at the position corresponding to each of the scanning steps s has information relating to the transmittance wavelength which differs among the pixel arrays of each image. This arrangement enables to obtain images each having a different spectral sensitivity among the pixels by a simplified or an efficient computation process based on the information relating to the transmittance wavelength which differs solely depending on a pixel column direction, not both on a pixel column direction and on a pixel row direction, which contributes to a high-speed computation process.

The embodiment can take the following modifications.

(A) In the embodiment, the single wedge band pass filter, namely, the WBPF 12 having a spectral transmittance characteristic that a transmittance wavelength of light differs depending on the transmittance site of the light is moved for scanning to capture images and to obtain spectral characteristic information relating to the wavelength range necessary for each pixel so as to reduce the size and the production cost of the two-dimensional spectroradiometer 1 and to shorten the measurement time thereof. In the embodiment, this technique is applied to measurement of the light source L. This technique is applicable to a system for measuring a two-dimensional spectral reflectance of a sample or a two-dimensional color reflectance of the sample based on the spectral reflectance by providing an illuminator for illuminating the sample. Also, the technique is applicable to a microspectrophotometry or luminescence microspectrophotometry. In any case, the arrangement contributes to size reduction, the production cost reduction, and shortening of the measurement time of the two-dimensional spectroradiometer.

(B) In the embodiment, the two imaging planes i.e. the first imaging plane 2b and the second imaging plane 6b are formed by providing the objective optical system 2 and the relay optical system comprised of the relay lens 6, respectively. The WBPF 12 of the scanning WBPF 10, and the image sensor 7 are disposed spaced away from each other by arranging the scanning WBPF 12 near the first imaging plane 2b, and by arranging the image sensor 7 on the second imaging plane 6b, respectively. Alternatively, the image sensor 7 and the WBPF 12 may be disposed with respect to a single imaging plane without providing the relay optical system.

(C) In the embodiment, after a dark image is captured by blocking light by the first light blocking portion 112 at the position corresponding to the scanning step s=0, the filter support plate 11, specifically the WBPF 12 is moved in the plus x-direction each time the scanning step s is performed. Conversely, a dark image may be captured by blocking light by the second light blocking portion 113 at the position corresponding to the scanning step s=0, and the filter support plate 11 may be moved in the minus x-direction for scanning.

(D) In the embodiment, the response image $(F_{MN})_{ij}(\lambda)$ is obtained in advance by actual measurement for storage. Alternatively, it is possible to obtain a response image by implementing a predetermined estimative computation or a like calculation for storage without performing the actual measurement.

(E) The configuration of the WBPF 12 may be the one other than the wedge, in which the filter thickness is linearly changed in the scanning direction, namely, front and rear transmittance surfaces are made flat, such as a configuration in which the filter thickness is formed curvedly, namely, a transmittance surface is curved.

(F) In the embodiment, scanning is performed by moving the wedge-shaped WBPF 12 in one direction. Alternatively, it is possible to use a round-shaped BPF or other shaped BPF having an arc-shaped portion such as a semi circle, in which the filter thickness, namely, the transmittance wavelength is changed in a circumferential direction of the filter, and to rotate the BPF relative to the light rays La, namely, around the optical path each time the scanning step is performed for scanning.

As described above, a two-dimensional spectroradiometer comprises: an optical system which receives light from an object to be measured to form an optical image; a transmittance wavelength variable filter having a spectral transmittance characteristic that a transmittance wavelength of the light differs depending on a transmittance site of the transmittance wavelength variable filter where the light is passed; a scanner which movably holds the transmittance wavelength variable filter on an optical path forming the optical image for sequential scanning at a plurality of scanning positions; and an image sensor which captures the optical image composed of the light passing through the transmittance wavelength variable filter at each of the scanning positions of the filter to acquire a plurality of images having a different spectral sensitivity among pixels of the image at the each of the scanning positions.

In the above arrangement, the optical image is formed by causing the optical system to receive the light from the object to be measured. The transmittance wavelength variable filter has the spectral transmittance characteristic that the transmittance wavelength of the light differs depending on the transmittance site of the filter where the light is passed. The scanner scannably holds the filter on the optical path forming the optical image. The image sensor captures the optical image composed of the light passing through the filter at the each of the scanning positions of the filter, and the image having the different spectral sensitivity among the pixels is acquired at the each of the scanning positions.

In this way, the plurality of images with each one having a different spectral sensitivity among the pixels are acquired at the respective scanning positions. Specifically, the pixels of the image acquired by the image sensor at the each of the scanning positions are composed of light having a different spectral characteristic depending on the transmittance site, namely, at the each of the scanning positions, not of light of the same transmittance wavelength, namely, of light of the same spectral characteristic. This arrangement enables to obtain spectral characteristic information relating to the wavelength range necessary for each pixel by moving the single transmittance wavelength variable filter for scanning, in other words, to obtain plural images each having a different spectral sensitivity among the pixels by using the single transmittance wavelength variable filter. Thereby, the number of filters necessary for scanning is remarkably reduced, and as the number of filters is reduced, the scanning load and the moving distance i.e. the scanning distance of the scanner are minimized. This enables to reduce the size and the production cost of the two-dimensional spectroradiometer, and to shorten the measurement time, which makes it possible to realize a handy two-dimensional spectroradiometer.

Preferably, the scanner may perform the scanning by moving the transmittance wavelength variable filter in one direction on an imaging plane of the optical image relative to the light forming the optical path.

In the above arrangement, the scanner performs the scanning by moving the filter in the one direction on the imaging plane of the optical image relative to the light forming the optical path. This arrangement enables to acquire the plural images each having a different spectral sensitivity among the pixels using the filter with a simplified arrangement of moving the filter in the one direction on the imaging plane of the optical image, which contributes to further shortening of the scanning time, namely, the measurement time.

Preferably, the optical system may include an objective optical system which receives the light from the object to be measured to form a first optical image, and a relay optical system which relays the first optical image to form a second optical image; and the transmittance wavelength variable filter may be arranged near an imaging plane of the first optical image, and the image sensor may be arranged on an imaging plane of the second optical image.

In the above arrangement, the transmittance wavelength variable filter is arranged near the imaging plane of the first optical image formed by the objective optical system, and the image sensor is arranged on the imaging plane of the second optical image formed by the relay optical system. This arrangement enables to dispose the filter away from the image sensor, to suppress stray light due to plane reflection between the filter and the image sensor, and to construct the image sensor without a possibility of interference with the filter.

Preferably, the transmittance wavelength variable filter may include a light blocking portion for blocking the light from an imaging area of the image sensor where the optical image is formed, the light blocking portion being formed on both or one of side portions of the transmittance wavelength variable filter in a scanning direction thereof.

In the above arrangement, the light blocking portion for blocking the light from the imaging area of the image sensor where the optical image is formed is formed on both or one of the side portions of the filter in the scanning direction thereof. This arrangement enables to move the filter by the scanner for scanning, and at the same time to obtain information relating to each pixel as a dark image, which is obtained by blocking the light by the light blocking portion of the filter. Thereby, the two-dimensional spectroradiometer can be produced with a simplified arrangement without the need of additionally providing a light blocker for performing dark image correction and a scanner for moving the light blocker for scanning.

Preferably, the transmittance wavelength variable filter may include a wedge band pass filter having a characteristic that a central wavelength of the light passing each of the transmittance sites of the filter is sequentially varied in a scanning direction of the filter.

In the above arrangement, the transmittance wavelength variable filter includes the wedge band pass filter having the characteristic that the central wavelength of the light passing each of the transmittance sites of the filter is sequentially varied in the scanning direction of the filter. This arrangement enables to easily realize an arrangement of obtaining plural images each having a different spectral sensitivity among the pixels by moving the wedge band pass filter in the scanning direction.

Preferably, the images captured by the image sensor at the respective scanning positions of the filter may have information relating to the transmittance wavelength which is varied in correlation to the central wavelength sequentially varied in the scanning direction of the filter with respect to each pixel array of each of the images.

In the above arrangement, the images obtained at the respective scanning positions have the information relating to the transmittance wavelength different from each other with respect to each pixel array of each of the images. This arrangement enables to obtain images each having a different spectral sensitivity among the pixels by a simplified or efficient computation process based on the information relating to the transmittance wavelength which differs solely depending on a pixel column direction, not both on a pixel column direction and on a pixel row direction, which contributes to a high-speed computation process.

As described above, in a method for measuring a two-dimensional spectral luminance of an object by a two-dimensional spectroradiometer provided with an optical system which receives light from the object to be measured to form an optical image, a transmittance wavelength variable filter having a spectral transmittance characteristic that a transmittance wavelength of the light differs depending on a transmittance site of the transmittance wavelength variable filter where the light is passed; and an image sensor which captures the optical image composed of the light passing through the transmittance wavelength variable filter, the method comprises the steps of sequentially moving the transmittance wavelength variable filter relative to an optical path forming the optical image for sequential scanning at a plurality of scanning positions; and capturing the optical image composed of the light passing through the transmittance wavelength variable filter at each of the scanning positions of the filter to acquire a plurality of images having a different spectral sensitivity among pixels of the image at the each of the scanning positions.

Preferably, the scanning may be performed by moving the transmittance wavelength variable filter in one direction on an imaging plane of the optical image relative to the light forming the optical path.

Preferably, the transmittance wavelength variable filter may include a wedge band pass filter having a characteristic that a central wavelength of the light passing each of the transmittance sites of the filter is sequentially varied in a scanning direction of the filter.

Preferably, the images captured by the image sensor at the respective scanning positions of the filter may have information relating to the transmittance wavelength which is varied in correlation to the central wavelength sequentially varied in the scanning direction of the filter with respect to each pixel array of each of the images.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

What is claimed is:

1. A two-dimensional spectroradiometer comprising:
   an optical system which receives light from an object to be measured to form an optical image;
   a transmittance wavelength variable filter having a spectral transmittance characteristic that a transmittance wavelength of the light differs depending on a transmittance site of the transmittance wavelength variable filter where the light is passed;
   a scanner which movably holds the transmittance wavelength variable filter on an optical path forming the optical image for sequential scanning at a. plurality of scanning positions; and
   a two-dimensional image sensor which captures the optical image composed of the light passing through the transmittance wavelength variable filter at each of the scanning positions of the filter to acquire a plurality of images having a different spectral sensitivity among pixels of the image at the each of the scanning positions, wherein
   each image of the plurality of images is composed of a two-dimensional image,
   the each image of the plurality of images represents at least two lights having different wavelengths from one another depending on a pixel of the two-dimensional image sensor, and
   the wavelengths of the lights received by a certain pixel are different from one another depending on the each image.

2. The two-dimensional spectroradiometer according to claim 1, wherein the scanner performs the scanning by moving the transmittance wavelength variable filter in one direction on an imaging plane of the optical image relative to the light forming the optical path.

3. The two-dimensional spectroradiometer according to claim 1, wherein
   the optical system includes an objective optical system which receives the light from the object to be measured to form a first optical image, and a relay optical system which relays the first optical image to form a second optical image; and
   the transmittance wavelength variable filter is arranged near an imaging plane of the first optical image, and the image sensor is arranged on an imaging plane of the second optical image.

4. The two-dimensional spectroradiometer according to claim 1, wherein
   the transmittance wavelength variable filter includes a light blocking portion for blocking the light from an imaging area of the image sensor where the optical image is formed, the light blocking portion being formed on both or one of side portions of the transmittance wavelength variable filter in a scanning direction thereof.

5. The two-dimensional spectroradiometer according to claim 1, wherein
   the transmittance wavelength variable filter includes a wedge band pass filter having a characteristic that a central wavelength of the light passing each of the transmittance sites of the filter is sequentially varied in a scanning direction of the filter.

6. The two-dimensional spectroradiometer according to claim 5, wherein
   the images captured by the image sensor at the respective scanning positions of the filter have information relating to the transmittance wavelength which is varied in correlation to the central wavelength sequentially varied in the scanning direction of the filter with respect to each pixel array of each of the images.

7. A method for measuring a two-dimensional spectral luminance of an object comprising:
   receiving light from an object to measured to form an optical image using a two-dimensional spectroradiometer, where the two-dimensional spectroradiometer includes:
      a transmittance wavelength variable filter having a spectral transmittance characteristic that a transmittance wavelength of the light differs depending on a transmittance site of the transmittance wavelength variable filter where the light is passed; and,
      a two-dimensional image sensor that includes a pixel array;
   sequentially moving the transmittance wavelength variable filter relative to an optical path forming the optical image for sequential scanning at a plurality of scanning positions;
   capturing, with the two-dimensional image sensor, the optical image composed of the light passing through the transmittance wavelength variable filter at each of the scanning positions of the filter to acquire a plurality of images having a different spectral sensitivity among pixels of the image at the each of the scanning positions, where:

each image of the plurality of images is composed of a two-dimensional image.

the each image of the plurality of images represents at least two lights having different wavelengths from one another depending on a pixel of the two-dimensional image sensor, the wavelengths of the lights received by a certain pixel are different from one another depending on the each image, processing the captured images for the results of a measurement; and outputting the results of the measurement.

8. The two-dimensional spectral luminance measuring method according to claim 7, wherein the scanning is performed by moving the transmittance wavelength variable filter in one direction on an imaging plane of the optical image relative to the light forming the optical path.

9. The two-dimensional spectral luminance measuring method according to claim 7, wherein the transmittance wavelength variable filter includes a wedge band pass filter having a characteristic that a central wavelength of the light passing each of the transmittance sites of the filter is sequentially varied in a scanning direction of the filter.

10. The two-dimensional spectral luminance measuring method according to claim 9, wherein the images captured by the image sensor at the respective scanning positions of the filter have information relating to the transmittance wavelength which is varied in correlation to the central wavelength sequentially varied in the scanning direction of the filter with respect to each pixel array of each of the images.

* * * * *